United States Patent
Francis et al.

(10) Patent No.: US 11,504,208 B2
(45) Date of Patent: Nov. 22, 2022

(54) TOOL HOLDER AND SYSTEM

(71) Applicant: FREEHAND 2010 LIMITED, Guildford (GB)

(72) Inventors: Clive Francis, Guildford (GB); Daniel Barnett, Guildford (GB); David Pinto, Guildford (GB)

(73) Assignee: FREEHAND 2010 LIMITED, Guildford (GB)

( * ) Notice: Subject to any disclaimer, the term of this patent is extended or adjusted under 35 U.S.C. 154(b) by 196 days.

(21) Appl. No.: 16/612,123

(22) PCT Filed: May 10, 2018

(86) PCT No.: PCT/GB2018/051270
§ 371 (c)(1),
(2) Date: Nov. 8, 2019

(87) PCT Pub. No.: WO2018/206970
PCT Pub. Date: Nov. 15, 2018

(65) Prior Publication Data
US 2021/0077221 A1     Mar. 18, 2021

(30) Foreign Application Priority Data
May 11, 2017   (GB) ..................................... 1707577

(51) Int. Cl.
*A61B 90/50*     (2016.01)
*A61B 34/30*     (2016.01)
(52) U.S. Cl.
CPC .............. *A61B 90/50* (2016.02); *A61B 34/30* (2016.02); *A61B 2034/301* (2016.02); *A61B 2090/506* (2016.02); *A61B 2090/508* (2016.02)
(58) Field of Classification Search
CPC .............. A61B 90/50; A61B 2090/506; A61B 2090/508
See application file for complete search history.

(56) References Cited

U.S. PATENT DOCUMENTS

| 5,649,956 A * | 7/1997 | Jensen | B25J 9/1065 606/1 |
|---|---|---|---|
| 2012/0088963 A1 | 4/2012 | Yasunaga | |
| 2014/0052155 A1 | 2/2014 | Hourtash | |

FOREIGN PATENT DOCUMENTS

| DE | 10 2013 222005 | 4/2015 |
|---|---|---|
| DE | 102013222005 | 4/2015 |

(Continued)

OTHER PUBLICATIONS

International Search Report and Written Opinion, International Application No. PCT/GB2018/051270, PCT/ISA/210, PCT/ISA/237, dated Oct. 18, 2018.

(Continued)

*Primary Examiner* — Phong Son H Dang
(74) *Attorney, Agent, or Firm* — Saliwanchik, Lloyd & Eisenschenk

(57) ABSTRACT

A tool holder for use as a surgical assistant, the tool holder including: first and second beam members; a frame; at least one linkage member coupled to the frame and the first and second beam members; a mounting configuration to hold a tool, the mounting configuration being coupled to the first and second beam members; and a drive mechanism mounted with respect to the frame, wherein the at least one linkage member and the mounting configuration are coupled to the first and second beam members in a parallelogram configuration, the drive mechanism is configured to drive a tilt movement of the mounting configuration with respect to the frame by movement of the first beam member with respect to the second beam member to orient the mounting configuration to a tilt angle, and the drive mechanism is configured to drive a pan movement of the tool about a pan axis, the drive mechanism being further configured to orient the pan axis with respect to the frame dependent on the tilt angle.

14 Claims, 37 Drawing Sheets

(56) References Cited

FOREIGN PATENT DOCUMENTS

| JP | 61-297092 | 12/1986 |
| JP | 11-507252 | 6/1999 |
| JP | 2002-530209 | 9/2002 |

OTHER PUBLICATIONS

Japanese Patent Application No. 2020-512928, Official Notice of Rejection, dated Mar. 15, 2022, 6 pages.

\* cited by examiner

TOOL HOLDER AND SYSTEM

CROSS-REFERENCE TO RELATED APPLICATIONS

This application is a national stage application of International Application No. PCT/GB2018/051270, filed May 10, 2018, which claims priority to Great Britain Application No. 1707577.1, filed May 11, 2017, the disclosures of both of which are incorporated herein by reference in their entirety, including any figures, tables, and drawings.

Embodiments of the present invention relate to a tool holder which may be a robotic tool assistant. In particular, some embodiments relate to a robotic assistant configured to support and maneuver a surgical tool, such as an endoscope or other endoscopic tool.

During a surgical operation involving endoscopic tool (often referred to as "keyhole surgery"), a surgeon will typically support and maneuver one or more surgical tools in order to perform one or more tasks at a surgical site within the patient. The surgeon is presented with a view of the surgical site (or at least part of the surgical site) through a display screen which is located within a field of view of the surgeon (e.g. within an operating theatre in which the operation is being performed).

The image displayed on the display screen is typically captured by an endoscope but may include images acquired from other sources—images which may have been captured earlier before the operation or during the operation (e.g. MRI images, x-rays, or images from an earlier operation).

The image which is displayed on the display screen and captured by, for example, an endoscope is generally a live image, in that it is an image of the surgical site (or part thereof) in real-time—although it will be appreciated that the image may be a video image which can be paused during an operation.

The endoscope which may be used to capture such live images has historically been supported by a human assistant. Human assistants are often relatively expensive (e.g. being a junior surgeon) and cannot hold the endoscope steady during the operation. Furthermore, the human assistant is takes up valuable space around the patient.

To alleviate some of these issues robotic surgical assistants have been developed. Some such robotic surgical assistants are extremely complex devices with a large number of moving joints and a need for complex kinematic calculations to achieve even relatively simple movements of the endoscope. Some such robotic surgical assistants have attempted to simplify the control and complexity issues and still achieve desired and intuitive movements of the endoscope under control of the surgeon. However, these simplified robotic surgical assistants commonly require some compromises. For example, some robotic surgical assistants are relatively large and block large parts of the space adjacent the patient in at least some configurations, some need to be placed on the patient and so limit access to the patient, some require complex restraint mechanisms to avoid injury to the patient (e.g. by tearing of an incision site), and some do not achieve natural and intuitive movements in all configurations.

Whilst these problems are prevalent in relation to surgical operations, similar problems exist in other fields in which it is necessary to support a tool (especially when the tool must be supported relatively steadily for relatively long periods of time). For example, such fields may include mechanical engineering in relation to large or complex machines and/or the nuclear industry (in which access is normally limited).

There is a need, therefore, to alleviate one or more of the problems associated with the prior art.

Accordingly, an aspect of the present invention provides a tool holder for use as a surgical assistant, the tool holder including: first and second members; a frame; at least one linkage member coupled to the frame and the first and second beam members; a mounting configuration to hold a tool, the mounting configuration being coupled to the first and second beam members; and a drive mechanism mounted with respect to the frame, wherein the at least one linkage member and the mounting configuration are coupled to the first and second beam members in a parallelogram configuration, the drive mechanism is configured to drive a tilt movement of the mounting configuration with respect to the frame by movement of the first beam member with respect to the second beam member to orient the mounting configuration to a tilt angle, and the drive mechanism is configured to drive a pan movement of the tool about a pan axis, the drive mechanism being further configured to orient the pan axis with respect to the frame dependent on the tilt angle.

The at least one linkage member may include a first and a second linkage member.

The tool holder may further include: one or more brake elements configured to inhibit or substantially prevent movement of the at least one linkage member with respect to the frame.

The drive mechanism may further include at least one drive motor to drive the pan movement and tilt movement.

The at least one drive motor may be a single motor to drive both the pan and tilt movements.

The tool holder further include a mode changing motor which is configured to change a mode of operation at least one drive motor between a tilt mode of operation and a pan mode of operation.

The mode changing motor may be associated with a brake element of the drive mechanism which is configured to brake movement of at least part of the drive mechanism when not in a mode changing mode of operation.

The tool holder may further including a mode selection arm which is drivable, by the drive mechanism, between a first position associated with the tilt movement and a second position associated with the pan movement.

The mode selection arm may be coupled to a carriage member which is configured for rotation with respect to the mode selection arm.

A brake element of the drive mechanism may be associated with the carriage member and may be configured to provide selective braking of the rotational movement between the mode selection arm and the carriage member.

The carriage member may be configured for rotation with respect to the mode selection arm about a first carriage axis and the carriage member defines a second carriage axis, the second carriage axis being a pan axis about which the pan movement occurs.

The tool holder may further include a slide mechanism coupled to the carriage member and the first beam member, wherein the slide mechanism may be configured for rotation about the second carriage axis.

The slide mechanism may be configured to vary in length between the coupling to the carriage member and the first beam member.

Each of the at least one linkage member may be coupled to the frame via a joint mechanism.

The joint mechanism may be configured to permit rotational movement of the coupled linkage member with respect to the frame about at least two axes.

The two axes may be perpendicular to each other.

The mounting configuration may include a tool receiving portion to receive the tool and at least one tool driving mechanism to drive a movement of the tool with respect to the tool receiving portion.

The at least one tool driving mechanism may be configured to drive one or both of a zoom or a rotational movement of the tool with respect to the tool holder.

The tool holder may further include the tool.

The tool may be an endoscopic instrument.

The endoscopic instrument may be an endoscope.

Another aspect provides a system including a tool holder, wherein the system further includes a control unit configured to control the operation of the drive mechanism.

The control unit may further include a user input subsystem which is configured to receive a user input, the control unit being configured to control the operation of the drive mechanism based, at least in part, on the received user input.

Another aspect provides a tool holder for use as a surgical assistant, the tool holder including: a frame; a mounting configuration coupled to the frame to hold a tool; a mounting shaft carrying the frame; and a drive mechanism, wherein the drive mechanism is configured for rotation with the frame and with respect to the mounting shaft, and the drive mechanism is configured to drive both a pan and a tilt operation of the mounting configuration.

Another aspect provides a tool holder for use as a surgical assistant, the tool holder including: a frame; a mounting configuration coupled to the frame to hold a tool; a mounting shaft carrying the frame; and a stop mechanism, wherein: the frame is configured to rotate with respect to the mounting shaft, the stop mechanism includes a first stop member fixed for rotation with the mounting shaft, a second stop member fixed for rotation with the frame, and a third stop member, and the third stop member is configured for rotation with respect to the first stop member through a first range of motion and with respect to the second stop member through a second range of motion, such that the stop mechanism limits a range of motion of the frame with respect to the mounting shaft to a range defined by a combination of the first and second ranges of motion.

The stop mechanism may limit the range of motion of the frame with respect to the mounting shaft to a range greater than 360 degrees.

The tool holder may further include a first beam member, a second beam member, a first linkage member, a second linkage member, wherein the coupling of the mounting configuration to the frame is via the first and second beam members and the first and second linkage members.

Embodiments of the present invention are described, by way of example only, with reference to the accompanying drawings, in which.

Figure 22:
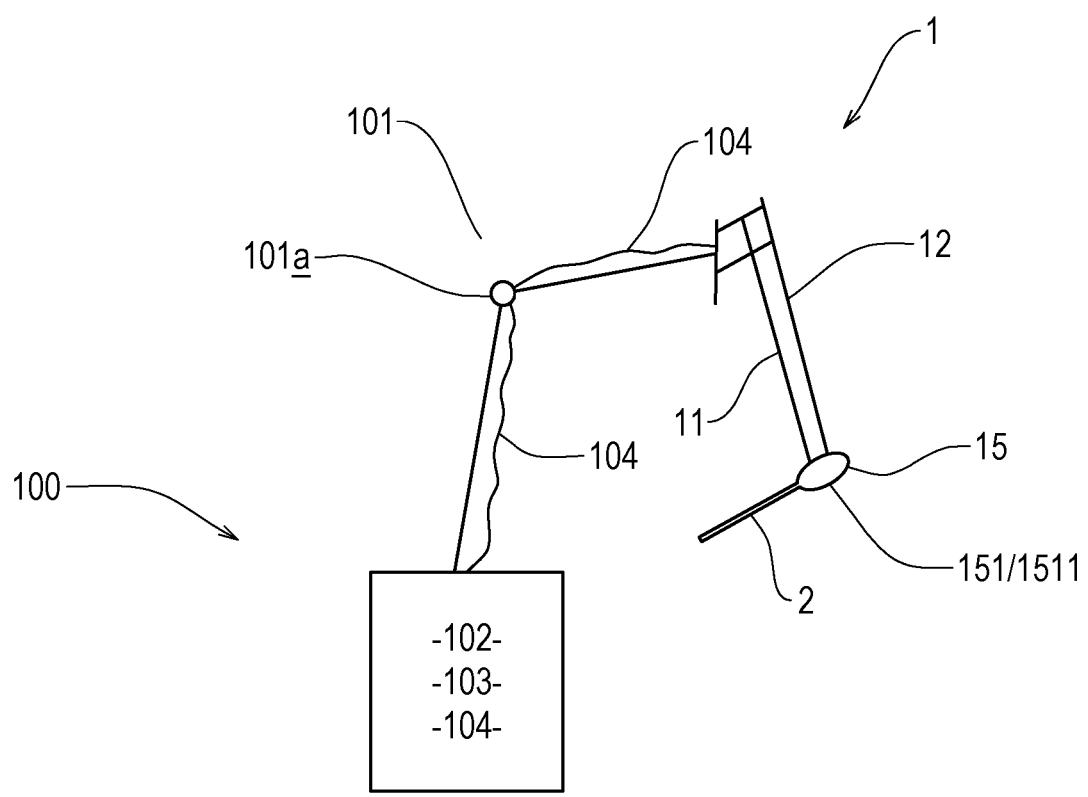
FIG. 22 shows an embodiment of a surgical assistant.
Figure 23:
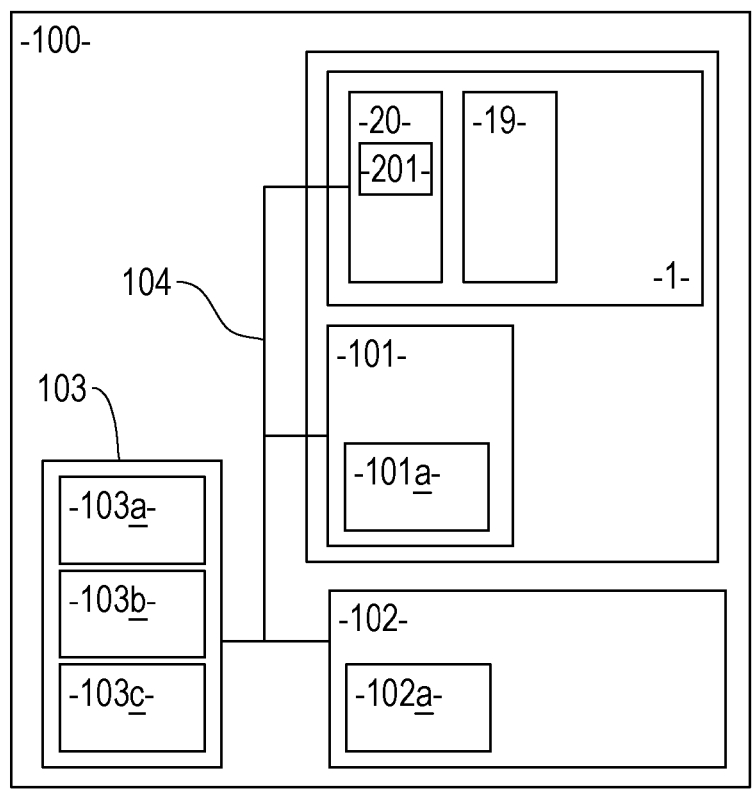
FIG. 23 shows a system according to some embodiments.
Figure 24:
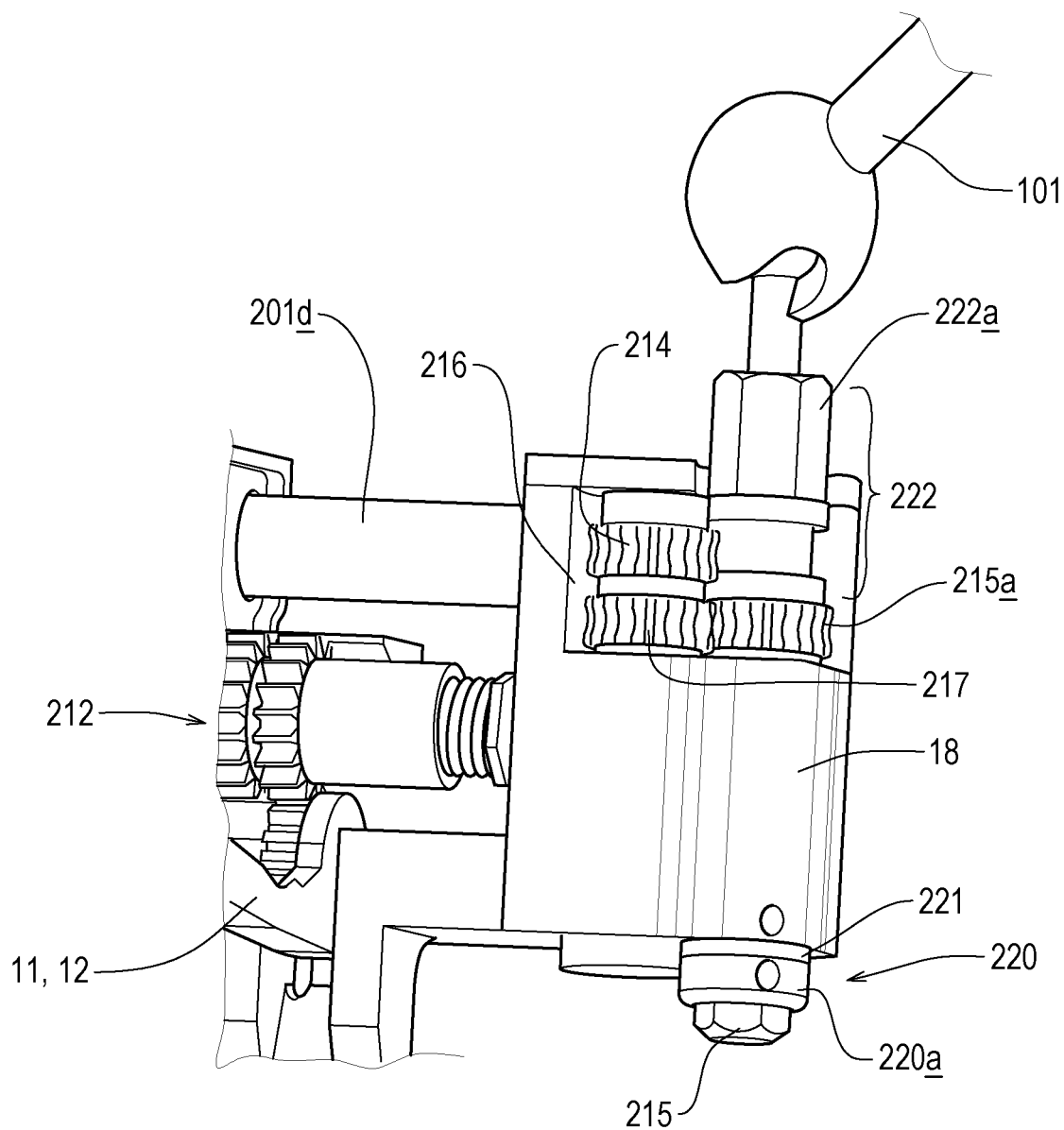
FIG. 24 shows part of an embodiment of a surgical assistant.

With reference to FIGS. 22 and 23, embodiments of the present invention include a robotic assistant 1 configured to support and maneuver a tool 2. In some embodiments, the robotic assistant 1 is a surgical robotic assistant 1 which is configured to support and maneuver a surgical tool 2.

In some such embodiments, the surgical tool 2 is an endoscopic surgical tool 2 which may be an endoscope or other viewing instrument. The endoscopic surgical tool 2 may be configured to interact with the surgical site—e.g. the endoscopic surgical tool may be forceps, a clamp, or the like. The endoscopic surgical tool 2 may include a light pipe.

The robotic assistant 1 may be part of a wider system 100 (of which the tool 2 may also form a part).

The wider system 100 may include an arm 101 which is configured to support the robotic assistant 1. The arm 101 may have a distal end which is attached (or configured to be attached) to a part of the robotic assistant 1 and a proximal end which is attached (or configured to be attached) to another structure. The arm 101 may include one or more joints 101a along its length. The or each joint 101a may be configured to allow one part of the arm 101 to move with respect to another part of the arm 101 about the joint 101a. The joint 101a may have a first mode of operation in which such movement is permitted (i.e. in which the joint 101a does not substantially inhibit such movement) and a second mode of operation in which such movement is substantially inhibited or prevented. The second mode of operation may, therefore, be a locked mode and the first mode may be an unlocked mode.

The arm 101 (e.g. the joint 101a) may include a user operable control which is configured, when actuated, to change the mode of operation of the joint 101a—if there is more than one joint 101a then more than one user operable control may be provided (e.g. one for each joint 101a) or one user operable control be control more than one joint 101a (and one user operable control may control all joints 101a of an arm 101. In other words, the arm 101 may include one or more user actuatable lockable joints 101a.

The proximal end of the arm 101 may include a first mounting arrangement which is configured to mate with a corresponding mounting arrangement of the structure to which it may be attached. The first mounting arrangement may, for example, allow removable attachment between the arm 101 and the structure (meaning that the arm 101 can be secured to the structure and removed (and re-secured) without damage to the mounting arrangements).

In some embodiments, the structure to which the proximal end of the arm 101 may be attached may be a stand which includes one or more ground engaging elements (such as wheels or casters) which are configured to engage a floor surface. In such embodiments, the structure may include a vertically extending support between the one or more ground engaging elements and the mounting arrangement.

In some embodiments, the structure to which the proximal end of the arm 101 may be attached may be a clamp which is configured to be secured (e.g. removably) to a rail such as a rail typically found at the edge of a surgical table or a ceiling mounted rail.

The system 100 may include a power supply unit 102 which is configured to be connected in electrical communication with a power supply such as a battery 102a (which may form part of the power supply unit 102 in some embodiments) or a mains power supply. The power supply unit 102 may also be configured to be connected in electrical communication with a control unit 103 of the system 100 and, ultimately, with one or more parts of the surgical assistant 1.

The power supply unit 102 is configured to provide electrical power from a power source (such as the battery 102a or mains power supply) to the surgical assistant 1 in order to power the operation thereof.

The control unit 103 is configured to control the operation of one or more parts of the surgical assistant 1—as described herein. In some embodiments, this control includes the selective delivery of electrical power to one or more motors of the surgical assistant 1. Accordingly, in some embodiments, the control unit 103 is coupled in electrical communication with the power supply unit 102 and the surgical assistant 1.

The control unit 103 includes a user input sub-system 103a which is configured to receive one or more inputs from a user (e.g. a surgeon or other operator) and to determine one or more desired movements of the surgical assistant 1 based on the one or more inputs. The control unit 103 may be configured to drive one or more operations of the surgical assistant 1 based on the determined one or more desired movements of the surgical assistant 1, seeking to achieve the or each desired movement. Accordingly, the one or more desired movements may be considered to be one or more instructed movements.

The user input sub-system 103a may take a number of different forms. In some embodiments, the user input sub-system 103a includes one or more manually operated controls (e.g. one or more levers and/or switches) which are configured to be operated by a hand or foot of the user. In some embodiments, the user input sub-system 103a is a hands-free sub-system in which the sub-system 103a can be operated without requiring the user to manipulate controls with their hands. Such a hands-free sub-system may include a detector which is configured to detect movement of a part of the user (such as their head, hands, feet, legs, eyes, arms, or the like). The detector may include an image recognition unit configured to capture images of the user, to detect a part of the user, and to track that part of the user between images in order to detect movement. The detector may include an emitter detection unit which is configured to detect the position and/or orientation of an emitter which is attached to the user (the emitter may be a beam emitter which is configured to output a beam of electromagnetic radiation such as a laser beam). The detector may be configured to be attached to the user and to detect movement of a part of the user using, for example, one or more accelerometers. The detector may then communicate this detected movement to another part of the control unit 103 via a wired or wireless communication link.

The distal end of the arm 101 may include a second mounting arrangement which is configured to mate with a corresponding mounting arrangement of the surgical assistant 1 to which it may be attached. The second mounting arrangement may, for example, allow removable attachment between the arm 101 and the robotic assistant (meaning that the arm 101 can be secured to the assistant 1 and removed (and re-secured) without damage to the mounting arrangements).

In some embodiments, the system 100 includes a wiring loom 104 which is configured to connect the control unit 103 (if provided) and one or more parts of the robotic assistant 1 (such as one or more motors thereof) in electrical communication. In some embodiments, the wiring loom 104 is configured to connect the power supply unit 102 in electrical communication with the one or more parts of the robotic assistant 1. The wiring loom 104 may include one or more cables which are coupled to the arm 101, for example.

Figure 20:
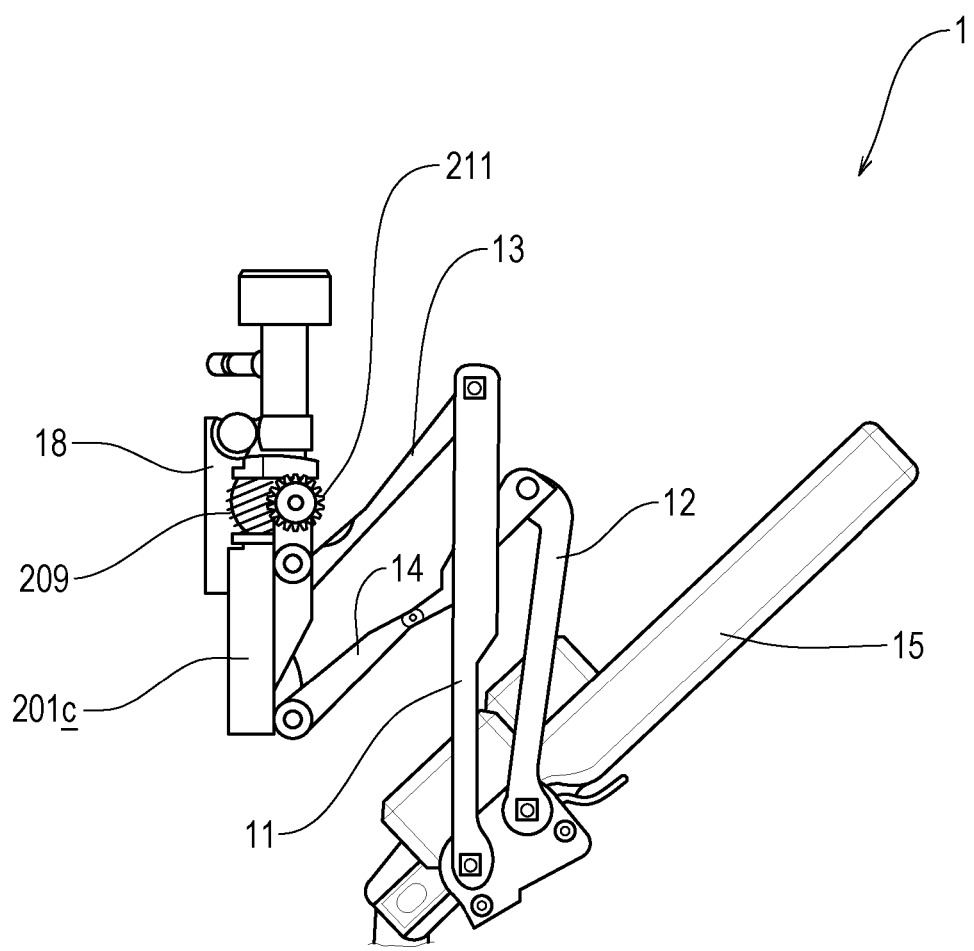
FIGS. 20 and 21 show some embodiments of a surgical assistant.
Figure 21:
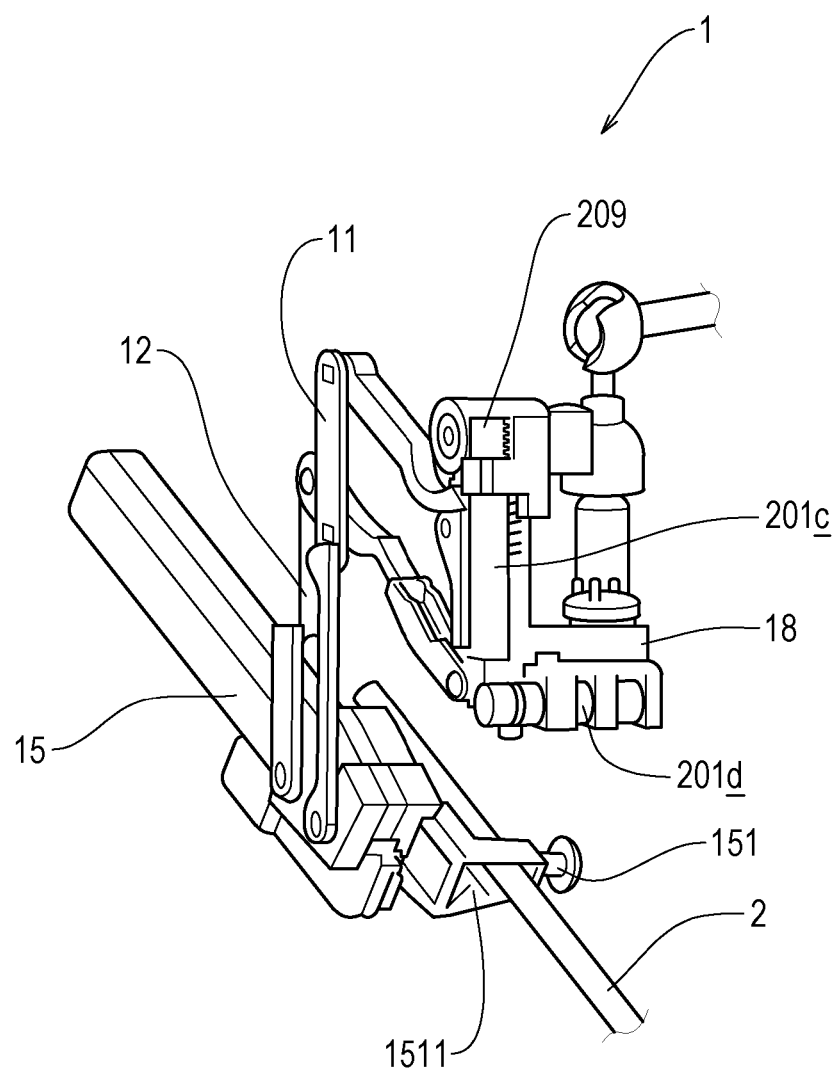

Embodiments of the robotic assistant 1 are now described with reference to FIGS. 1-21 (noting that FIGS. 20 and 21 relate to embodiments of a generally different form to those of FIGS. 1-19).

In accordance with some embodiments, the robotic assistant 1 includes a first and a second beam member 11,12. The first and second beam members 11,12 are respective substantially elongate members which extend along respective first and second axes. The first beam member 11, therefore, extends along the first axis, which is a central longitudinal axis of the first beam member 11. Similarly, the second beam member 12 extends along the second axis, which is a central longitudinal axis of the second beam member 12.

The first and second beam members 11,12 may be substantially straight members but, in some embodiments, may include one or more bends. Accordingly, the first and second axes may represent the general direction of extension of the first and second beam members 11,12 respectively.

The first and second beam members 11,12 are constrained in a substantially parallel arrangement. Accordingly, the first and second axes are constrained to remain substantially parallel to each other. In other words, an angular relationship between the first and second beam members 11,12 may be constrained.

In some embodiments, this constraint is provided by a first and a second linkage member 13,14. The first linkage member 13 may be located towards a proximal end of each of the first and second beam members 11,12 and the second linkage member 14 may be located towards a distal end of the first and second beam members 13,14 relative to the first linkage member 13.

The first linkage member 13 may be attached or otherwise coupled to the first beam member 11 and the second beam member 12 by respective first and second pivotable couplings 13a,13b.

The first pivotable coupling 13a of the first linkage member 13 may couple the first linkage member 13 to the first beam member 11 such that the first beam member 11 is pivotable about a first linkage member first axis. The first linkage member first axis is substantially perpendicular to the first axis and the second axis.

The second pivotable coupling 13b of the first linkage member 13 may couple the first linkage member 13 to the second beam member 12 such that the second beam member 12 is pivotable about a first linkage member second axis. The first linkage member second axis is substantially perpendicular to the first axis and the second axis.

In some embodiments, the first and second pivotable coupling 13a,13b of the first linkage member 13 only permits rotation of the first and second beam members 11,12 with respect to the first linkage member 13 about the first linkage member first and second axes and constrain (i.e. substantially prevent) rotation of the first and second beam members 11,12 with respect to the first linkage member 13 about any other axes.

The second linkage member 14 may be similarly arranged. Accordingly, the second linkage member 14 may be attached or otherwise coupled to the first beam member 11 and the second beam member 12 by respective first and second pivotable couplings 14a,14b.

The first pivotable coupling 14a of the second linkage member 14 may couple the second linkage member 14 to the first beam member 11 such that the first beam member 11 is pivotable about a second linkage member first axis. The second linkage member first axis is substantially perpendicular to the first axis and the second axis.

The second pivotable coupling 14b of the second linkage member 14 may couple the second linkage member 14 to the second beam member 12 such that the second beam member 12 is pivotable about a second linkage member second axis. The second linkage member second axis is substantially perpendicular to the first axis and the second axis.

In some embodiments, the first and second pivotable coupling 14a,14b of the second linkage member 14 only permits rotation of the first and second beam members 11,12 with respect to the second linkage member 14 about the second linkage member first and second axes and constrain (i.e. substantially prevent) rotation of the first and second beam members 11,12 with respect to the second linkage member 14 about any other axes.

The first linkage member first axis and the second linkage member first axis may be parallel with each other, and spaced apart from each other along a length of the first beam member 11.

The first linkage member second axis and the second linkage member second axis may be parallel with each other, and spaced apart from each other along a length of the second beam member 12.

The distance between the first and second pivotable couplings 13a,13b of the first linkage member 13 may be generally equal to the distance between the first and second pivotable couplings 14a,14b of the second linkage member 13. In other words, the distance between the first linkage member first and second axes may be generally equal to the distance between the second linkage member first and second axes.

The first and second linkage members 13,14 may extend along respective first and second linkage member longitudinal axes and may be generally elongate in form.

As will be appreciated, therefore, the first and second beam members 11,12 and first and second linkage members 13,14, may form a parallelogram arrangement in which the first and second beam member 11,12 remain parallel with each other and the first and second linkage members 13,14 remain parallel with each other, as the beam members 11,12 rotate with respect to the linkage members 13,14. The first and second beam members 11,12 may be moved closer or further apart from each other by rotation about the pivotable couplings 13a,13b,14a,14b. Such movement causes movement of one of the beam members 11,12 with respect to the other in the direction of the first and second axes (as well as moving the first and second axes closer or further apart from each other). Thus, distal ends 11a,12a of the first and second beam members 11,12 will also move with respect to each other.

In some embodiments, the robotic assistant includes a mounting configuration 15. The mounting configuration 15 is configured to secure the tool 2 to the robotic assistant 1 (or to the rest of the robotic assistant 1 if the tool 2 is a part thereof).

The mounting configuration 15 may be coupled to both the first and second beam members 11,12 by first and second pivotable couplings 15a,15b of the mounting configuration 15—much like the first and second linkage members 13,14.

The mounting configuration 15 may be attached or otherwise coupled to the first beam member 11 and the second beam member 12 by respective first and second pivotable couplings 15a,15b.

The first pivotable coupling 15a of the mounting configuration 15 may couple the mounting configuration 15 to the first beam member 11 such that the first beam member 11 is pivotable about a mounting configuration first axis. The mounting configuration first axis is substantially perpendicular to the first axis and the second axis.

The second pivotable coupling 15b of the mounting configuration 15 may couple the mounting configuration 15 to the second beam member 12 such that the second beam member 12 is pivotable about a mounting configuration second axis. The mounting configuration second axis is substantially perpendicular to the first axis and the second axis.

In some embodiments, the first and second pivotable coupling 15a,15b of the mounting configuration 15 only permits rotation of the first and second beam members 11,12 with respect to the mounting configuration 15 about the mounting configuration first and second axes, and constrain (i.e. substantially prevent) rotation of the first and second beam members 11,12 with respect to the mounting configuration 15 about any other axes.

The first linkage member first axis, the second linkage member first axis, and the mounting configuration first axis may be parallel with each other, and spaced apart from each other along a length of the first beam member 11.

The first linkage member second axis, the second linkage member second axis, and the mounting configuration second axis may be parallel with each other, and spaced apart from each other along a length of the second beam member 12.

The distance between the first and second pivotable couplings 13a,13b,14a,14b of the first and/or second linkage members 13,14 may be generally equal to the distance between the first and second pivotable couplings 15a,15b of the mounting configuration 15. In other words, the distance between the first and/or second linkage member first and second axes may be generally equal to the distance between the mounting configuration first and second axes.

The mounting configuration 15 may extend along respective a mounting configuration longitudinal axis and may be generally elongate in form.

Accordingly, as will be understood, the mounting configuration 15 may act as a further linkage member—similar to the first and second linkage members 13,14.

The mounting configuration 15 (unlike the first and second linkage members 13,14 in some embodiments) may include a tool receiving portion 151 which is configured to receive at least part of a tool 2 to secure the tool 2 with respect to the mounting configuration 15.

The tool receiving portion 151 may include, for example, a clamp member which defines an aperture which is configured to receive part of a tool. In some embodiments, the tool receiving portion 151 includes a tool driving mechanism 1511. The tool driving mechanism 1511 may be configured to drive rotation of a tool received by the tool receiving portion 151 in at least one movement with respect to the mounting configuration 15. This movement may be a rotational movement (i.e. rotation of the tool 2 about a longitudinal axis thereof) and/or a zoom movement (i.e. movement of the tool 2 along a longitudinal axis thereof). In some embodiments, the tool driving mechanism 1511 is configured to drive both rotational and zoom movements of the tool 2 with respect to the mounting configuration 15.

The tool driving mechanism 1511 may include, therefore, one or more motors, which may be electrical motors. In some embodiments, the tool driving mechanism 1511 may include a driven wheel which is configured to engage (directly or indirectly) a part of the tool 2 such that rotation of the driven wheel (as driven by one of the one or more motors, for example) will cause movement of the tool 2. In some embodiments, there may be more than one such driven wheels and there may be at least two driven wheels which drive movement of the tool 2 in different directions (e.g. rotational movement and zoom movement. In embodiments with more than one driven wheel, the different movements (e.g. rotational and zoom) may operate independently of each other—such that one driven wheel does not does not prevent the movement of the tool 2 driven by the other driven wheel. This may be achieved by, for example, allowing the tool 2 to slip with respect to a driven wheel when the tool 2 moves in a direction which that driven wheel does not drive. Other arrangements to achieve movement of the tool 2 with respect to the mounting configuration 15 are possible according to some embodiments. Indeed, in some embodiments, the mounting configuration 15 does not provide such movements.

As will be understood, therefore, the robotic assistant 1 may be configured to drive movement of a tool 2 coupled to the mounting configuration 15 by movement of the first and second beam members 11,12 with respect to each other (closer together or further apart). This movement can be described as a tilt movement. The movement itself can be achieved by moving either of the first and second beam members 11,12 along the first and second axes respectively, with respect to the other of the first and second beam members 11,12.

In some embodiments, the mounting configuration 15 is effectively cantilevered from the distal ends of the first and second beam members 11,12 and the tool 2 extends therefrom. The tool 2 may, in practice, be inserted into a port member (such as a laparoscopic port used in surgical operations) but the port member does not constrain or control movement of the tool 2, in some embodiments. Accordingly, the movements of the tool 2 as described herein under the control of the robotic assistant 1 may be considered to be movements which can be achieved by the robotic assistant 1 in free space. As will be understood from the description herein elsewhere, the movement may be about a single confocal or goniometric point.

As will be understood, the mounting configuration 15 may be located remotely from the first and second linkage members 13,14, with the mounting configuration 15 distanced from the second linkage member 14 by a length of the first and second beam members 11,12.

The first and second linkage members 13,14 have been described above insofar as their respective distal ends are concerned. The first and second linkage members 13,14 are each generally elongate members. Proximal ends of each of the first and second linkage members 13,14 may be generally aligned with the respective distal ends thereof such that the first and second linkage members 13,14 extend along the first and second linkage member longitudinal axes respectively.

Accordingly, each of the first and second linkage members 13,14 has a respective length (from the distal to the proximal ends thereof). The length of the first linkage member 13 may be generally equal to the length of the second linkage member 14.

The first and second linkage member longitudinal axes are substantially parallel to each other, and are constrained to remain parallel to each other during operation of the robotic assistant 1.

The first and second linkage members 13,14 are attached (or otherwise coupled) to respective first and second joint mechanisms 16,17. The first and second joint mechanisms 16,17 are also attached (or otherwise coupled) to a frame 18 of the robotic assistant 1.

The first joint mechanism 16 couples the first linkage member 13 to the frame 18 and the second joint mechanism 17 couples the second linkage member 14 to the frame 18.

The first and second joint mechanisms 16,17 need not be identical. In some embodiments, one of the first and second joint mechanisms 16,17 is a braked joint mechanism. In some embodiments, some embodiments, the other of the first and second joint mechanisms 16,17 is a free joint mechanism. In some embodiments, such as the depicted embodiment, it is the second joint mechanism 17 which is the braked joint mechanism and the first joint mechanism 16 which is the free joint mechanism, although this is just an example. In some embodiments, both the first and second joint mechanisms 16,17 are braked joint mechanisms.

A free joint mechanism is a joint mechanism which allows free movement around its pivot axis or axes. A braked joint mechanism is a joint mechanism which may selectively restrain (or "brake") movement around one or more pivot axes.

A free joint mechanism is described with reference to the depicted embodiments and the first joint mechanism 16 for ease of reference (but applies to the second joint mechanism 17 if that were a free joint mechanism).

The first joint mechanism 16 may be a generally universal joint. A first part 16a of the first joint mechanism 16 is coupled to the frame 18 and is configured to rotate with respect thereto about a first joint mechanism first axis. The first part 16a may comprise a generally cylindrical member with a longitudinal axis which extends along the first joint mechanism first axis.

The first part 16a may be coupled to the frame 18 at a proximal end thereof.

Towards a distal end of the first part 16a there may be a pivotable mounting which is configured to secure (in a pivotable manner) a yoke 13c of the first linkage member 13 (the yoke 13c being located at or towards the proximal end of the first linkage member 13) to the distal end of the first part 16a. Accordingly, a portion of the first part 16a may be located between parts of the yoke 13c of the first linkage member 13. The yoke 13c is configured to rotate with respect to the first part 16a about a first joint mechanism second axis. The yoke 13c is given as an example only and other pivotable coupling arrangements could equally be used.

A main part of the first linkage member 13 may extend from the yoke 13c thereof to the distal end of the first linkage member 13. The first linkage member 13 may be substantially rigid from the yoke 13c to the distal end thereof.

In some embodiments or interpretations, the yoke 13c of the first linkage member 13 may be considered to be a part of the first joint mechanism 16 rather than part of the first linkage member 13. Accordingly, the yoke 13c might be viewed as a second part 16b of the first joint mechanism 16.

As will be appreciated, the first joint mechanism first and second axes are generally perpendicular with respect to each other and may intersect each other. As will also be appreciated, rotation of the first part 16a of the first joint mechanism 16 with respect to the frame 18 will rotate the first joint mechanism second axis with respect to the frame 18 (about the first joint mechanism first axis).

A braked joint mechanism is described with reference to the depicted embodiments and the second joint mechanism 17 for ease of reference (but applies to the first joint mechanism 16 if that were a free joint mechanism).

The second joint mechanism 17 is a generally universal joint. A first part 17a of the second joint mechanism 17 is coupled to the frame 18 and is configured to rotate with respect thereto about a second joint mechanism first axis. The first part 17*a* may comprise a generally cylindrical member with a longitudinal axis which extends along the second joint mechanism first axis.

The first part 17*a* may be coupled to the frame 18 at a proximal end thereof. Towards a distal end of the first part 17*a* there may be a pivotable mounting which is configured to secure (in a pivotable manner) a yoke 14*c* of the second linkage member 14 (the yoke 14*c* being located at or towards the proximal end of the second linkage member 14) to the distal end of the first part 17*a*. Accordingly, a portion of the first part 17*a* may be located between parts of the yoke 14*c* of the second linkage member 14. The yoke 14*c* is configured to rotate with respect to the first part 17*a* about a second joint mechanism second axis. The yoke 14*c* is, again, an example of a pivotable coupling arrangement and other arrangements could equally be used.

The first joint mechanism first axis and the second joint mechanism first axis may be substantially parallel with each other. The first joint mechanism second axis and the second joint mechanism second axis are generally aligned in the same plane and that plane is parallel to the first and second axes.

A main part of the second linkage member 14 may extend from the yoke 14*c* thereof to the distal end of the second linkage member 14. The second linkage member 14 may be substantially rigid from the yoke 14*c* to the distal end thereof.

In some embodiments or interpretations, the yoke 14*c* of the second linkage member 14 may be considered to be a part of the second joint mechanism 17 rather than part of the second linkage member 14. Accordingly, the yoke 14*c* might be viewed as a second part 17*b* of the second joint mechanism 17.

As will be appreciated, the second joint mechanism first and second axes are generally perpendicular with respect to each other and may intersect each other. As will also be appreciated, rotation of the first part 17*a* of the second joint mechanism 17 with respect to the frame 18 will rotate the second joint mechanism second axis with respect to the frame 18 (about the second joint mechanism first axis).

The second joint mechanism 17 may include one or more brake elements 19, making the second joint mechanism 17 a braked joint mechanism.

The or each brake element 19 is configured to restrict, inhibit, or substantially prevent rotation of a part of the second joint mechanism selectively (generally referred to herein as braking).

A first 191 of the one or more brake elements 19 may be configured to brake rotation of the first part 17*a* of the second joint mechanism 17 with respect to the frame 18 (or another part of the second joint mechanism 17 which is secured to the frame 18). The first brake element 191 may, therefore, include a first portion which is fixed from rotation with respect to the frame 18 (and/or other part of the second joint mechanism 17) and a second portion which is fixed for rotation with the first part 17*a* of the second joint mechanism 17 (e.g. a shaft connected to the first part 17*a*).

The first and second portions of the first brake element 191 may be selectively engaged to restrict, inhibit, and/or prevent movement of the first portion with respect to the second portion. Accordingly, the first brake element 191 may be configured to be actuated between a first mode of operation in which the first and second portions move with respect to each other without substantive restriction, and a second mode of operation in which the first and second portions are engaged. With the first and second portions engaged, rotation of the first part 17*a* with respect to the frame 18 is braked. The first brake element 191 may, therefore, be a friction brake element.

The first brake element 191 may be secured to and held by the frame 18, as described herein.

A second 192 of the one or more brake elements 19 may be configured to brake rotation of the second part 17*b* of the second joint mechanism 17 with respect to the first part 17*a* (or of the yoke 14*c* with respect to the first part 17*a*, as will be understood). The second brake element 192 may, therefore, include a first portion which is fixed from rotation with respect to the first part 17*a* and a second portion which is fixed for rotation with the second part 17*b* (or yoke 14*c*). The first and second portions of the second brake element 192 may be selectively engaged to restrict, inhibit, and/or prevent movement of the first portion with respect to the second portion. Accordingly, the second brake element 192 may be configured to be actuated between a first mode of operation in which the first and second portions move with respect to each other without substantive restriction, and a second mode of operation in which the first and second portions are engaged. With the first and second portions engaged, rotation of the second part 17*b* (or yoke 14*c*) with respect to the first part 17*a* is braked. The second brake element 192 may, therefore, be a friction brake element.

The second brake element 192 may be secured to and held by the first part 17*a* of the second joint mechanism 17.

Accordingly, the first part 17*a* of the second joint mechanism 17 may, therefore, define a cavity or recess which is configured to receive at least a part of the second brake element 192. In some embodiments, the first part 17*a* of the second joint mechanism 17 may, therefore, have a yoke-like form (e.g. may be a first yoke) between the arms of which the second brake element 192 may be located. The second part 17*b* of the second joint mechanism 17 (or the yoke 14*c*) may be configured to receive the yoke-like form of the first part 17*a* of the joint mechanism 17 therebetween. Accordingly, the second part 17*b* of the second joint mechanism 17 (or the yoke 14*c*) may form a second yoke.

As will be understood, therefore, the rotation about the second joint mechanism 17 may be selectively braked by use of the or each brake element 19.

The frame 18 could take a number of different forms. In the depicted and some other examples, the frame 18 includes a first member or bar 181 to which the first and second joint mechanisms 16,17 may be attached. The first parts 16*a*,17*a* of these joint mechanisms 16,17 may be, therefore, located generally adjacent the first member or bar 181 of the frame 18. In some embodiments, the first joint mechanism 16 and the second joint mechanism 17 are attached to different parts of the frame 18.

In embodiments, including the first member or bar 181, the first member or bar 18 may define one or more apertures which are each configured to receive a shaft for rotation therewith. For example, one such shaft may belong to the first part 16*a* of the first joint mechanism 16 and another such shaft may belong to the first part 17*a* of the second joint mechanism 17. The or each aperture may also be configured to receive a bearing, for example (with the bearing configured to receive the shaft).

In the depicted embodiment, and some others, the frame 18 includes a second member or bar 182. The second member or bar 182 may be arranged substantially parallel to the first member or bar 181 of the frame 18. Like the first member or bar 181, the second member or bar 182 may also define one or more apertures each configured to receive a shaft and/or a bearing.

In some embodiments, the first and second members or bars 181,182 carry bearing housings 183 which are each configured to receive a shaft and/or bearing (e.g. for the first and/or second joint mechanism 16,17 as described above).

In some embodiments, such as the depicted embodiment, the frame 18 includes a brake element support member 184. The brake element support member 184 is configured to provide support for one or more of the one or more brake elements 19. In some embodiments, the brake element support member 184 is configured to support the first brake element 191. The brake element support member 184 may, therefore, be associated with the part of the frame 18 to which the second joint mechanism 17 is attached (and/or the first joint mechanism 16 if that is also a braked joint mechanism, and the description of the brake element support member 184 should be construed accordingly).

The brake element support member 184 may include an arm which is secured to a part of the frame 18 which opposes the attachment of the second joint mechanism 17. Accordingly, the brake element support member 184 may be attached to the first member or bar 181 and/or to the second member or bar 182. The brake element support member 184 may define a space between a part of the rest of the frame 18 (e.g. the first or second member or bar 181,182) and itself, which is configured to receive at least part of one of the brake elements 19—such as the first brake element 191. The brake support member 184 may be configured to support the brake element 19 (e.g. the first brake element 191) such that a shaft of the first part 17a of the second joint mechanism 17 extends through the brake element 19 supported thereby (the shaft may have, for example, passed through the first and/or second member or bar 181,182 and/or a bearing housing 183, and may be received by an aperture defined by the brake element support member 184 (which may also receive a bearing)).

As depicted, the first and second members or bars 181, 182, the brake element support member 184, and the or each bearing housing 183, all form part of a lower section of the frame 18. Clearly, the orientation of the frame 18 could be different in different embodiments and so this need not be the lower section in other embodiments or even in the same embodiment in a different orientation. Therefore, this lower section will also be referred to herein as the first section of the frame 18.

The frame 18 may include a second section which is depicted as an upper section (although, as explained, this need not be the case). Indeed, in some embodiments, the second section of the frame 18 is not attached to the first section but is supported with respect thereto in a substantially fixed position (e.g. the first and second sections of the frame 18 may be attached to some other structure such as a wall or another frame).

In the depicted and some other embodiments, the second section of the frame 18 carries (i.e. supports) a drive mechanism 20 for the robotic assistant 1.

The drive mechanism 20 includes at least one motor 201 which is configured to drive a movement of the first and second beam members 11,12—it being understood that the driving of one beam member 11,12 will cause the movement of the other beam member 12 not least due to the first and second linkage members 13,14 and/or the mounting configuration 15.

The drive mechanism 20 is configured, in some embodiments, to drive rotation of parts of the robotic assistant 1 around a first drive axis and/or a second drive axis, which in turn move the first and second beam members 11,12—as described in more detail below.

In some embodiments, such as the depicted embodiment, the drive mechanism 20 includes a first motor 201a and a second motor 201b. The first motor 201a is configured to operate as a mode changing motor and the second motor 201b is configured to drive movement of the first and second beam members 11,12—the mode changing motor determining what movement the second motor 201b drives.

The first motor 201a may be mounted on the second section of the frame 18—e.g. received by one or more mounting members 185 of the frame 18. The first motor 201a may be mounted such at a shaft thereof (the shaft which is rotated by operation of the first motor 201a) is generally parallel with the first and second axes.

The first motor 201a may be configured to rotate a first worm screw 202 (which is mounted to the aforementioned shaft of the first motor 201a). The first worm screw 202 is configured to mesh with a first worm wheel 203 which is mounted on a shaft which is held by the second section of the frame 18.

In some embodiments, a third member or bar 186 carries the or each mounting member 185 and extends generally parallel to the shaft of the first motor 201a. The third member or bar 186 may carry, at a part remote from the first section of the frame 18, the first worm wheel 203.

The first worm wheel 203 may be mounted on a shaft to the third member or bar 186. The first worm wheel 203 may be mounted for rotation with respect to the third member or bar 186 about an axis of the shaft.

The first worm wheel 203 may be coupled to a mode selection arm 204. The mode selection arm 204 may be coupled to the first worm wheel 203 for rotation therewith. Rotation of the first worm wheel 203 may, therefore, cause rotation of the mode selection arm 204 between a first mode position and a second mode position. This rotation may be driven, as will be appreciated, by the first motor 201a.

Accordingly, via this arrangement or another arrangement, the drive mechanism 20 may be configured to select a first mode of operation or a second mode of operation of the drive mechanism 20. In particular, in some embodiments, the first motor 201a is configured to select the first mode of operation or the second mode of operation. This selection may be achieved by operation of the first motor 201a to drive rotation of the mode selection arm 204 between the first mode position (corresponding with the first mode of operation of the drive mechanism) and the second mode position (corresponding with the second mode of operation of the drive mechanism).

The first mode of operation of the drive mechanism 20 may be tilt mode of operation and the second mode of operation of the drive mechanism 20 may be a pan mode of operation.

The mode selection arm 204 may be a generally L-shaped arm with a first portion extending away from the first worm wheel 203 generally radially with respect thereto (i.e. generally radially with respect to the shaft carrying the first worm wheel 203) and a second portion extending generally perpendicularly with respect to the first portion. The second portion may extend generally towards the first and second beam members 11,12.

The mode selection arm 204 and, in some embodiments a remote end of the second portion of the mode selection arm 204, may carry a carriage member 205 of the drive mechanism 20. The carriage member 205 may be carried for rotation with respect to the mode selection arm 204 about a first carriage axis.

In some embodiments, the mode selection arm 204 includes an annular piece at the remote end thereof. The annular piece may be configured to receive at least part of the carriage member 205 in some embodiments. The annular piece may receive a bearing, for example, which in turn receives the at least part of the carriage member 205.

The carriage member 205 has a first part which is coupled to the mode selection arm 204. It may be, therefore, a portion of the first part which is received by the distal end (e.g. the annular piece) of the mode selection arm 204. The first part may extend through the mode selection arm 204 and a portion of the first part of the carriage member 205 may be located on a first side of the mode selection arm 204.

In some embodiments, a third brake element 193 may be provided. This third brake element 193 may be part of the drive mechanism 20 or may be part of some other part of the surgical assistant 1. The third brake element 193 may be configured to be selectively engaged to restrict, inhibit, and/or prevent movement of the carriage member 205 with respect to the mode selection arm 204 about the first carriage axis. Accordingly, the third brake element 193 may be configured to be actuated between a first mode of operation in which the first and second portions thereof move with respect to each other without substantive restriction, and a second mode of operation in which the first and second portions are engaged. The first portion may be coupled for movement with the carriage member 205 and the second portion may be coupled for movement with the mode selection arm 204, for example. With the first and second portions engaged, rotation of the carriage member 204 with respect to the mode selection arm 204 is braked. The third brake element 193 may, therefore, be a friction brake element.

In some embodiments, the third brake element 193 is located in association with the first part of the carriage member 205 and may, therefore, be on the first side of the mode selection arm 204.

The carriage member 205 may include a second part which extends away from the mode selection arm 204 from a second side thereof (the second side opposing the first side across a depth of the mode selection arm 204). This second part may have a C-shaped section such that a portion of the carriage member 204 is then offset from the first carriage axis. A first part of the C-shaped section may be coupled to the second part of the carriage member 205. A second part of the C-shaped section, which opposes the first part across a height of the C-shaped section, may support a second worm wheel 206.

The second part of the C-shaped section may also support a fourth brake element 194. In some embodiments, this fourth brake element 194 is located on an outer portion of the second part of the C-shaped section, with the second worm wheel 206 located on an inner portion (i.e. closer to the part of the C-shaped section which links the first and second parts). The second part of the C-shaped section may define a second carriage axis. The first carriage axis may intersect the second worm wheel 206 and may be generally perpendicular to the second carriage axis.

The fourth brake element 194 may be part of the drive mechanism 20 or may be part of some other part of the surgical assistant 1. The fourth brake element 194 may be configured to be selectively engaged to restrict, inhibit, and/or prevent movement of the second worm wheel 206 with respect to the carriage member 205 about the second carriage axis. Accordingly, the fourth brake element 194 may be configured to be actuated between a first mode of operation in which the first and second portions thereof move with respect to each other without substantive restriction, and a second mode of operation in which the first and second portions are engaged. The first portion may be coupled for movement with the second worm wheel 206 and the second portion may be coupled for movement with carriage member 205, for example. With the first and second portions engaged, rotation of the second worm wheel 206 with respect to carriage member 204 is braked. The fourth brake element 194 may, therefore, be a friction brake element.

The drive mechanism 20 (or another part of the surgical assistant 1) may further include a slide mechanism 208. The slide mechanism 208 may be coupled for pivotable movement with respect to the carriage member 204. In some embodiments, the slide mechanism 208 is coupled for pivotable movement about the second carriage axis. In some embodiments, the slide mechanism 208 may be coupled to a part of the C-shaped section which opposes the second part thereof. The slide mechanism 208 may be so coupled by a proximal end thereof.

A distal end of the slide mechanism 208 may be coupled to the first or second beam member 11,12. This coupling may be via a universal joint 208a which may be a ball-joint. In some embodiments, the first or second beam member 11,12, as the case may be, defines and annular portion configured to receive a ball of the slide mechanism 208 to form the universal joint 208a. The annular portion may extend through a plane which is angled with respect to the first axis or the second axis (as the case may be) towards the slide mechanism 208.

The slide mechanism 208 could take a number of different forms but will include a proximal and a distal end which are such that the distance therebetween can be varied. Therefore, the slide mechanism 208 may include a first portion which includes the proximal end and a second portion which includes the distal end. The first and second portions may be configured for linear movement with respect to each other. The first and second portions may be restrained from rotational movement with respect to each other. The first portion could, for example, be in the form of a cylinder and the second portion could be, for example, in the form of a piston provided at least partially within the cylinder—such that the first and second portions are capable of linear telescopic movement. Such telescopic movement could, however, be provided with other configurations. An axis along which the slide mechanism extends, and can telescopically move, may intersect one or both of the first and second carriage axes.

The second motor 201b may be mounted for movement with the slide mechanism 208. As such, the second motor 201b may be mounted to the slide mechanism 208 (e.g. to the first portion thereof) and this mounting may be via one or more straps, for example. A rotor of the second motor 201b carries a second worm wheel 207 for rotation therewith (i.e. the second motor 201b is configured to drive rotation of the second worm wheel 207). The second worm wheel 207 is configured to mesh with the second worm gear 206.

The wiring loom 104 may couple each of the at least one motor 201 (i.e. first and second motors 201a,201b) to the power supply unit 102 and also to the control unit 103. The control unit 103 is configured to control the operation of the first and second motors 201a,201b and, in particular, whether each of the first and second motors 201a,201b are driven and the direction in which they are driven. As will be appreciated, the control unit 103 is configured to drive operation of the first and second motors 201a,201b independently of each other—i.e. they can be controlled to perform different respective operations.

The wiring loom 104 may also be coupled to the one or more brake elements 19 (i.e. first, second, third, and fourth brake elements 191,192,193,194) and couple the one or more brake elements 19 to the power supply unit 102 and/or the control unit 103.

In some embodiments, the one or more brake elements 19 may include at least one brake element (e.g. one of the first, second, third, and fourth brake elements 191,192,193,194) which is electrically operated or pneumatically operated or hydraulically operated. The control unit 103 may be configured to operate the one or more brake elements 19 and this may include, therefore, the controlling of the operation of one or more pumps, valves, actuators and the like.

The control unit 103 is configured to receive the user input from the user input sub-system 103a and to control the operation of the at least one motor 201 and the one or more brake elements 19 to active the user specified movement (which may be a user specified movement of the mounting configuration 15 and, therefore, may be a movement of the tool 2).

The control unit 103 may be configured to control a mode change operation.

A mode change operation may alter whether the operation of at least one of the at least one motors 201 causes a first type of movement or a second type of movement of the surgical assistant 1. The first type of movement may be a tilt movement or operation and the second type of movement may be a pan movement or operation. The terms "pan" and "tilt" refer, in general, to the movement experienced by the mounting configuration 15 (and, hence, the tool 2). The mode change operation, therefore, may be said to change the modes of operation of the drive mechanism 20.

In the depicted and some other embodiments, the first motor 201a determines which mode the drive mechanism 20 adopts. In particular, driving of the first motor 201a in a first direction may cause the drive mechanism to adopt the first (or tilt) mode and driving of the first motor 201a in a second direction may cause the drive mechanism to adopt the second (or pan) mode. As will be appreciated, driving the first motor 201a is a reference to driving the first worm screw 202 and, therefore, rotation of the first worm wheel 203.

In some embodiments, the first worm wheel 203 is coupled for movement with the mode selection arm 204. Therefore, operation of the first motor 201a in moves the mode selection arm 204 to determine whether the first or second mode is adopted.

In some embodiments, with the first portion of the mode selection arm 204 extending generally along an axis parallel to a rotor axis of the first motor 201a (i.e. such that the first carriage axis is generally parallel with the first and second main beams 11,12 and their axes), the first mode is selected. In the depicted embodiment, this can be seen in the figures in which the first portion of the mode selection arm 204 extends generally upwardly.

In this mode, the control unit 103 may actuate the second motor 201b to rotate the second worm screw 207. The control unit 103 may further actuate the fourth brake element 194 to be braked. As such, rotation of the second worm screw 207 causes movement of the slide mechanism 208 (to which the second motor 201b is secured) about the second carriage axis.

During this movement, the control unit 103 may be configured to actuate the third brake element 193 to its braked condition. The control unit 103 may be configured to actuate the first and second brake elements 191,192 to their unbraked conditions.

As such, in this mode, on actuation by the control unit 103 of the second motor 201b, rotation of the second worm screw 207 causes a rotational movement of the slide mechanism 208 about the second carriage axis, which causes a movement of the beam member 11,12 to which it is coupled (i.e. the first or the second beam member 11,12). This, in turn, causes movement of the other of beam member 11,12 (i.e. the other of the first and second beam member 11,12) and the mounting configuration 15.

Due to the orientation of the second carriage axis, this movement is a tilt operation of the mounting configuration 15.

In some embodiments, with the first portion of the mode selection arm 204 extending generally along an axis perpendicular to a rotor axis of the first motor 201a (i.e. such that the first carriage axis is generally perpendicular to the first and second main beams 11,12 and their axes), the second mode is selected. In the depicted embodiment, this can be seen in the figures in which the first portion of the mode selection arm 204 extends generally horizontally.

In this mode, the control unit 103 may actuate the second motor 201b to rotate the second worm screw 207. The control unit 103 may further actuate the fourth brake element 194 to be braked. As such, rotation of the second worm screw 207 causes movement of the slide mechanism 208 (to which the second motor 201b is secured) about the second carriage axis.

During this movement, the control unit 103 may be configured to actuate the third brake element 193 to its braked condition. The control unit 103 may be configured to actuate the first and second brake elements 191,192 to their unbraked conditions.

As such, in this mode, on actuation by the control unit 103 of the second motor 201b, rotation of the second worm screw 207 causes a rotational movement of the slide mechanism 208 about the second carriage axis, which causes a movement of the beam member 11,12 to which it is coupled (i.e. the first or the second beam member 11,12). This, in turn, causes movement of the other of beam member 11,12 (i.e. the other of the first and second beam member 11,12) and the mounting configuration 15.

Due to the orientation of the second carriage axis, this movement is a pan operation of the mounting configuration 15.

Once the mounting configuration 15 is a desired location (i.e. between movements), the control unit 103 is configured to actuate the first and second brake elements 191,192 to their braked conditions. This prevents movement of the first and second beam members 11,12 and so also prevents movement of the mounting configuration 15. This may be a locked mode for the surgical assistant 1 and/or the drive mechanism 20 (as opposed to an unlocked mode, when the first and second brake elements 191,192 are in their unbraked conditions).

The control unit 103 may be configured to implement the locked mode for the surgical assistant 1 and/or the drive mechanism 20 when movements of the tool 2 using the mounting configuration 15 are required (or may permit those movements during one or both of a tilt and pan operation). The control unit 103 may be configured to implement the locked mode during a change of mode.

In particular, whilst the two modes have been described above, the change of mode operation has not been described in detail.

The change of mode operation may be controlled by the control unit 103, which may be configured to actuate the first motor 201a to drive movement of the first worm screw 202 and, hence, drive rotation of the first worm wheel 203 and the coupled mode selection arm 204.

During this movement, as mentioned above, the control unit 103 may control activate the locked mode (i.e. may brake the first and second brake elements 191,192).

The control unit 103 may further unbrake the third and fourth brake elements 193,194. This allows the carriage member 205 to rotate with respect to the mode selection arm 204 and the slide mechanism 208 to rotate with respect to the carriage member 205 which, in turn, allows the correct orientation of the second carriage axis to be achieved.

Once the mode has been changed—i.e. the mode selection arm 204 has reached one of the two aforementioned positions—then the control unit 103 may perform one of the tilt and pan operations as described above.

In some embodiments, whilst waiting between pan and tilt operations, and when not in the locked mode, one or both of the third and fourth brake elements 193,194 may be braked.

In some embodiments, the mode change functionality is not provided and, instead, there may be two (or more) motors provided in place of the second motor 201*b*. Each such motor may be provided with further brake elements. Accordingly, instead of using a mode changing first motor 201*a* and a driving second motor 201*b*, multiple drive motors may be provided.

Some embodiments, seek to provide a true pan movement of the tool 2. In particular, many prior surgical assistants cannot provide a true left-to-right or right-to-left pan operation but, instead, provide an arcuate pan operation. In some prior assistants, the arc is small in some configurations but can be large in other configurations—e.g. when there is a high degree of tilt (i.e. with the tool 2 close to parallel with the axis of rotation). Embodiments seek to alleviate this issue.

In particular, embodiments seek to alleviate this issue by the provision of a second carriage axis which is not of a fixed orientation with respect to the first and second axes of the first and second beam members 11,12. This second carriage axis is the axis about which the pan movement is performed. Therefore, in some embodiments, this axis about which the pan movement is performed is varied depending on the current tilt position.

The second carriage axis may, therefore, be considered to be a pan axis. The drive mechanism 20 and, in particular, the carriage member 205 may be viewed as providing a pan axis orientation mechanism. This pan axis orientation mechanism is configured to orient the pan axis (and so the plane in which the pan movement occurs) dependent on a tilt angle (i.e. dependent on the angle of at least one of the slide mechanism 208, the first linkage member 13, the second linkage member 14, and the mounting configuration 15 with respect to the frame 18). The tilt angle may be defined as an angle between the frame 18 and at least one of the slide mechanism 208, the first linkage member 13, the second linkage member 14, and the mounting configuration 15 with respect to the frame 18. A steep tilt angle may be when the tool 2 is held at a low angle with respect to the frame 18 (i.e. a generally near vertical orientation when considering the embodiments in their depicted arrangements). A shallow tilt angle may be when the tool 2 is held at an angle close to perpendicular to the frame 18 (i.e. a generally near horizontal orientation when considering the embodiments in their depicted arrangements).

FIGS. 1 to 26 show a sequence of movements (or operations) of the surgical assistant 1.

Figure 1:
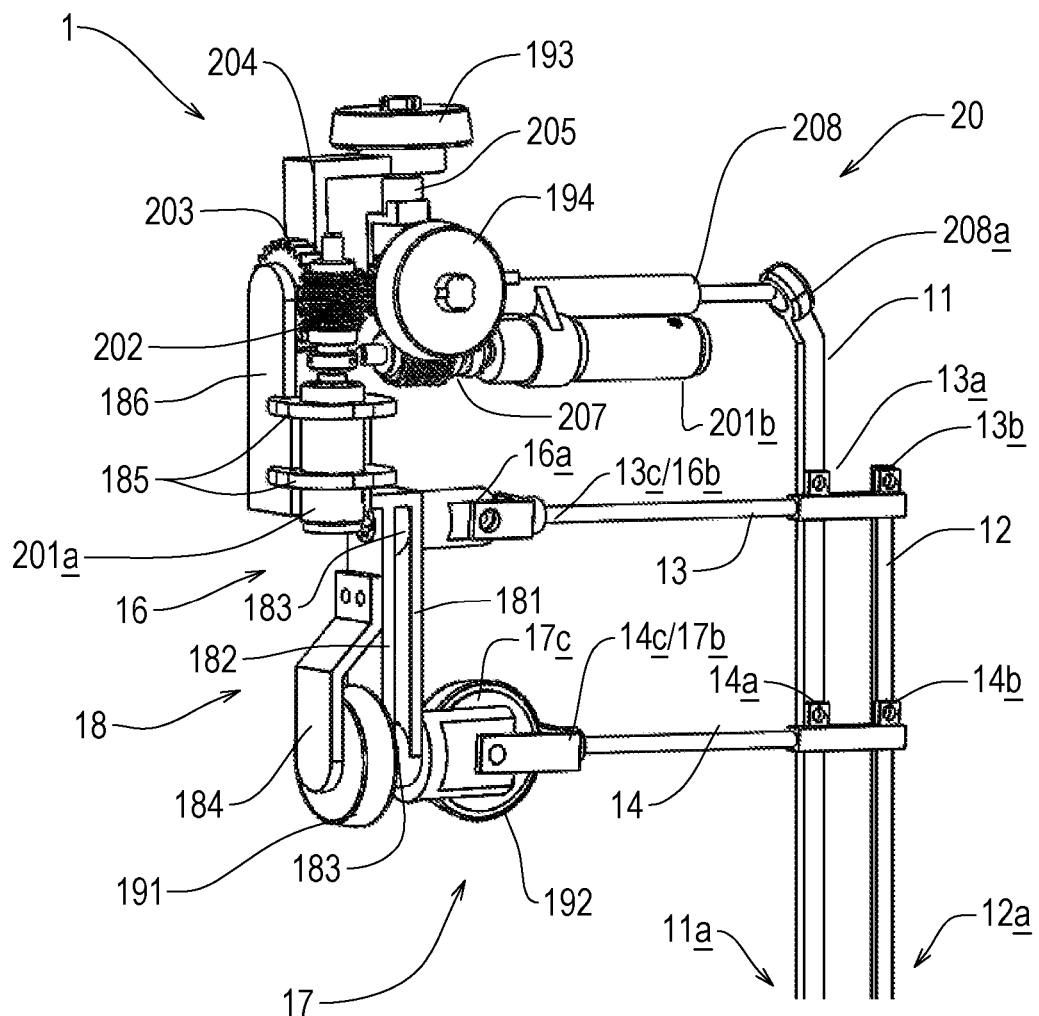
FIGS. 1-19 show some embodiments of at least part of a surgical assistant in various positions.
Figure 2:
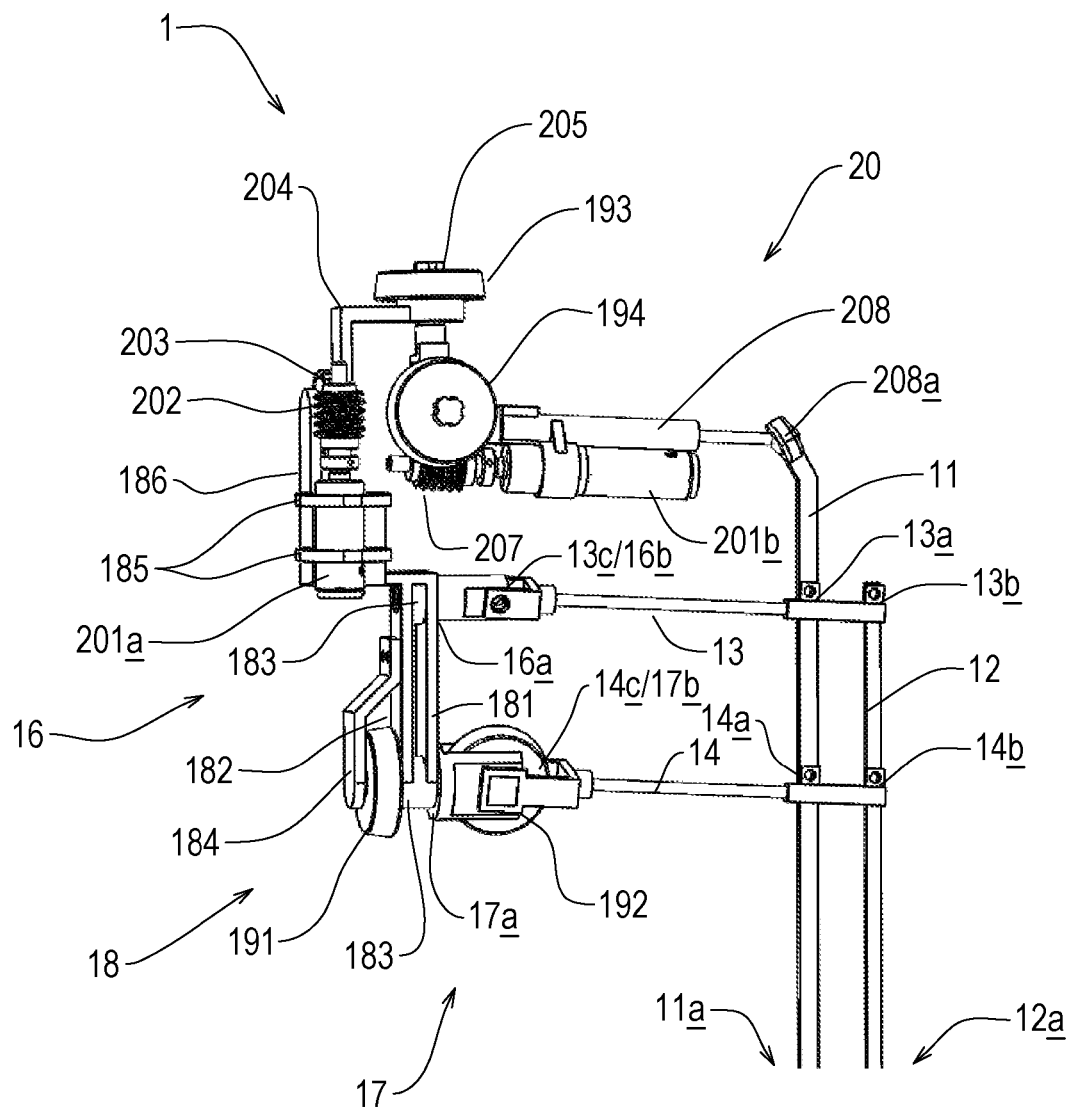

Therefore, in FIG. 1, the drive mechanism 20 (and so also the surgical assistant 1) is in a tilt mode of operation—as can be seen from the position of the mode selection arm 204. The second motor 201*b* is then driven to rotate the slide mechanism 208 about the second carriage axis. This movement can be seen by comparison of the orientation of the slide mechanism 208 between FIGS. 1 and 2.

As can also be seen, the first and second brake elements 191,192 are in their unbraked condition, and there is rotational movement about the first and second joint mechanisms 16,17, as the first and second linkage members 13,14 move with respect to the frame 18.

Figure 3:
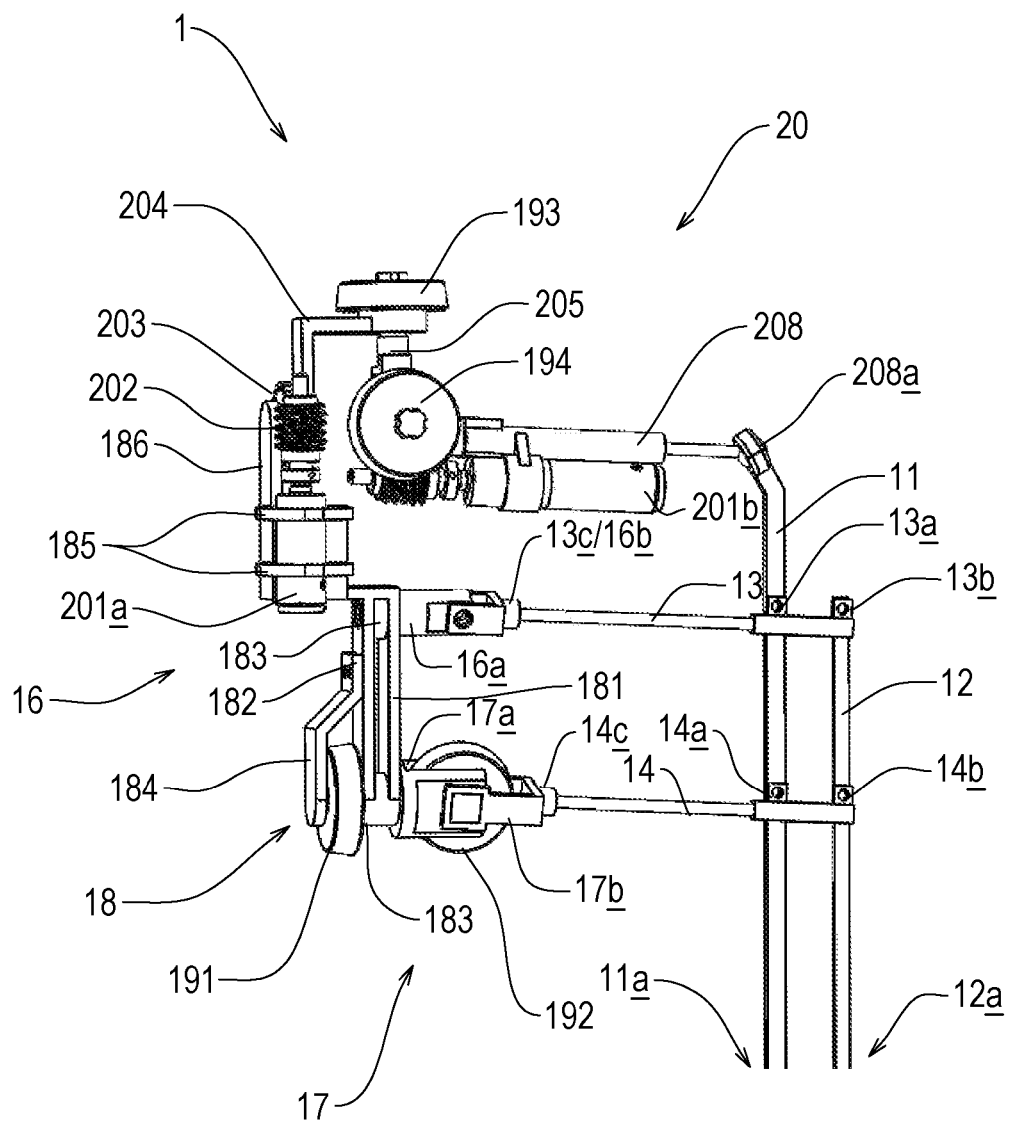

This tilt operation is continued as shown in FIG. 3.

Figure 4:
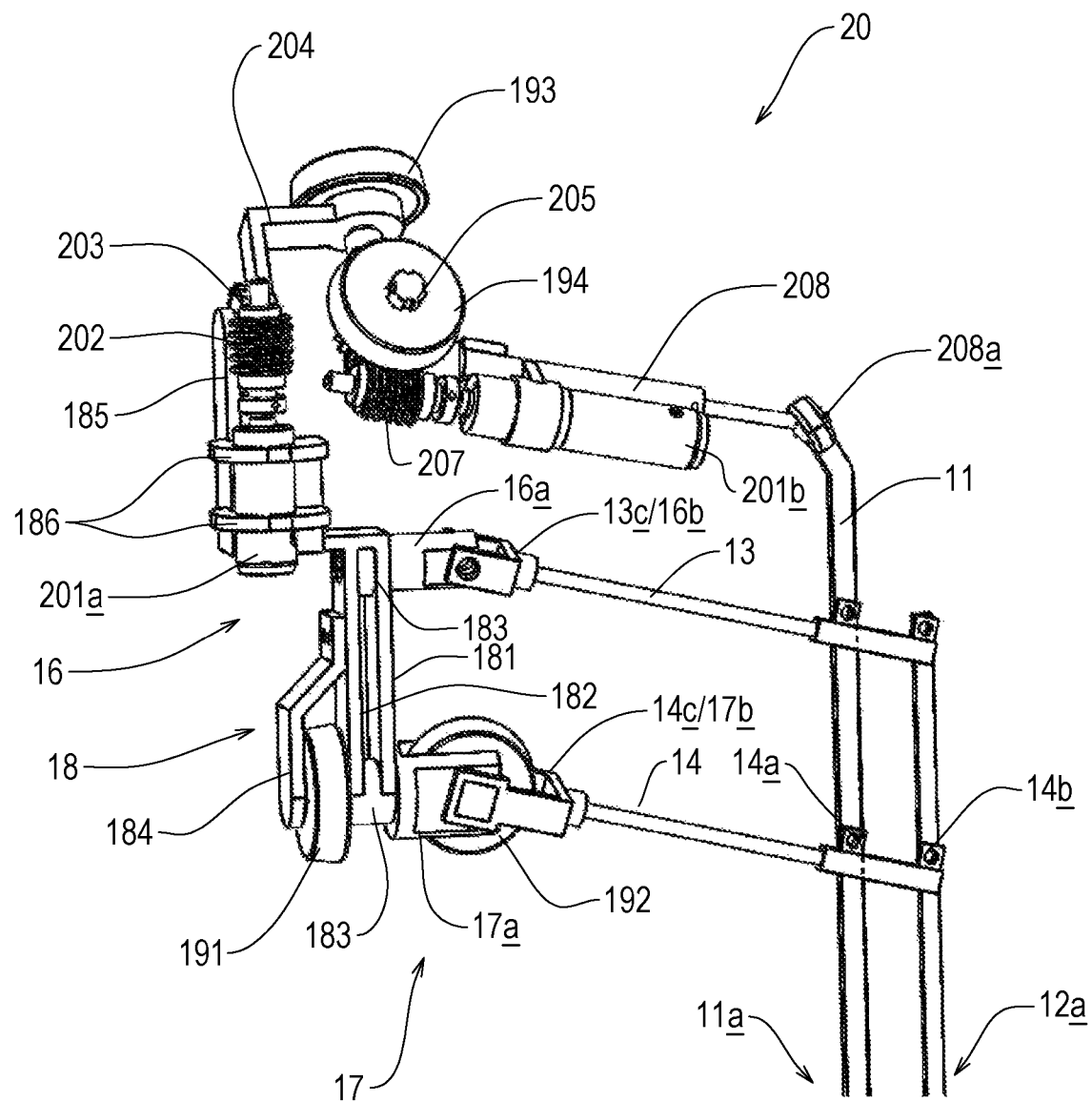

FIG. 4 shows the beginning of a change of mode operation from the tilt mode to the pan mode. Accordingly, as can be seen the mode selection arm 204 is rotated (e.g. by operation of the first motor 201*a*) with respect to the frame 18 to rotate the second carriage axis with respect to the frame 18. The third and fourth brake elements 193,194 are in their unbraked condition. However, to inhibit or substantially prevent movement of the mounting configuration 15, the first and second brake elements 193,194 are in their braked condition.

Figure 5:
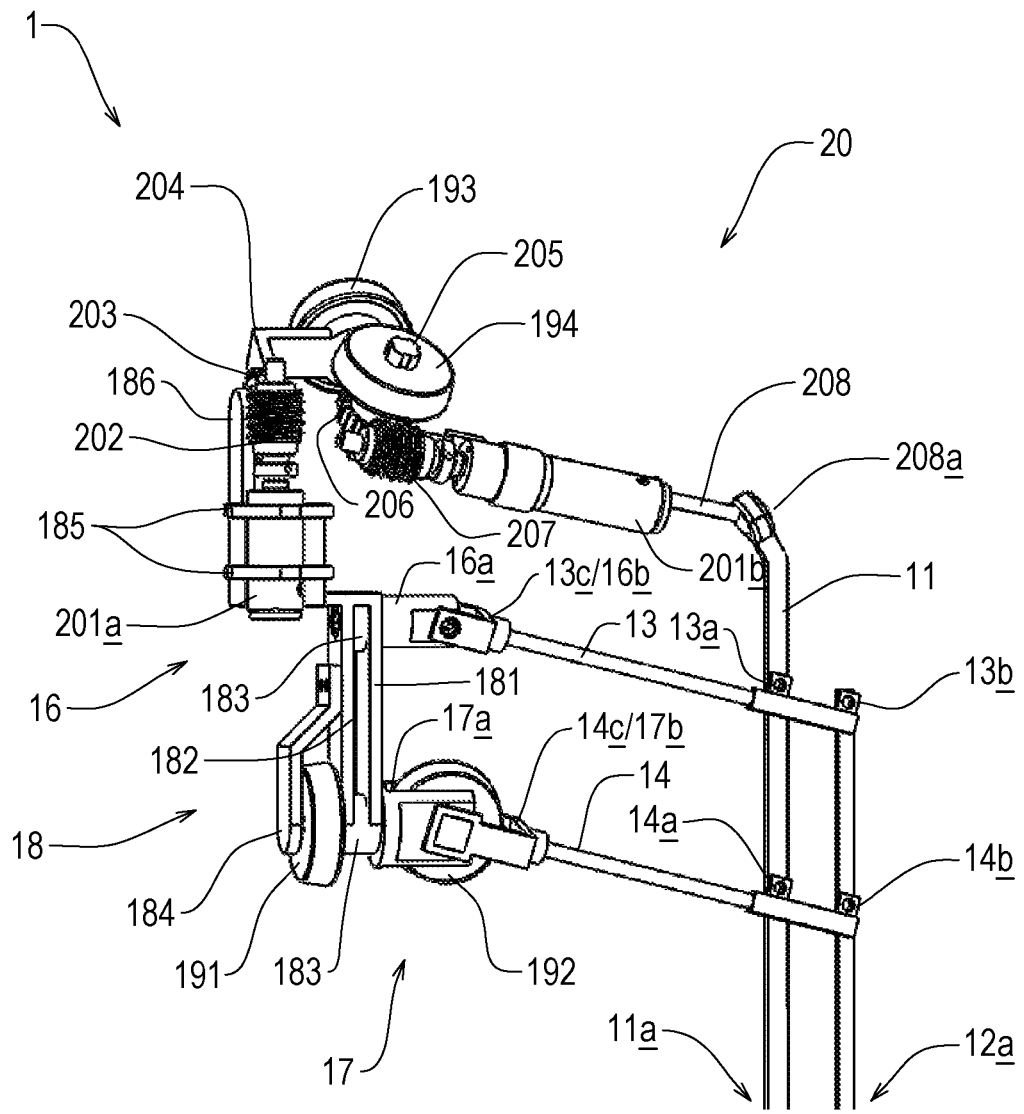
Figure 6:
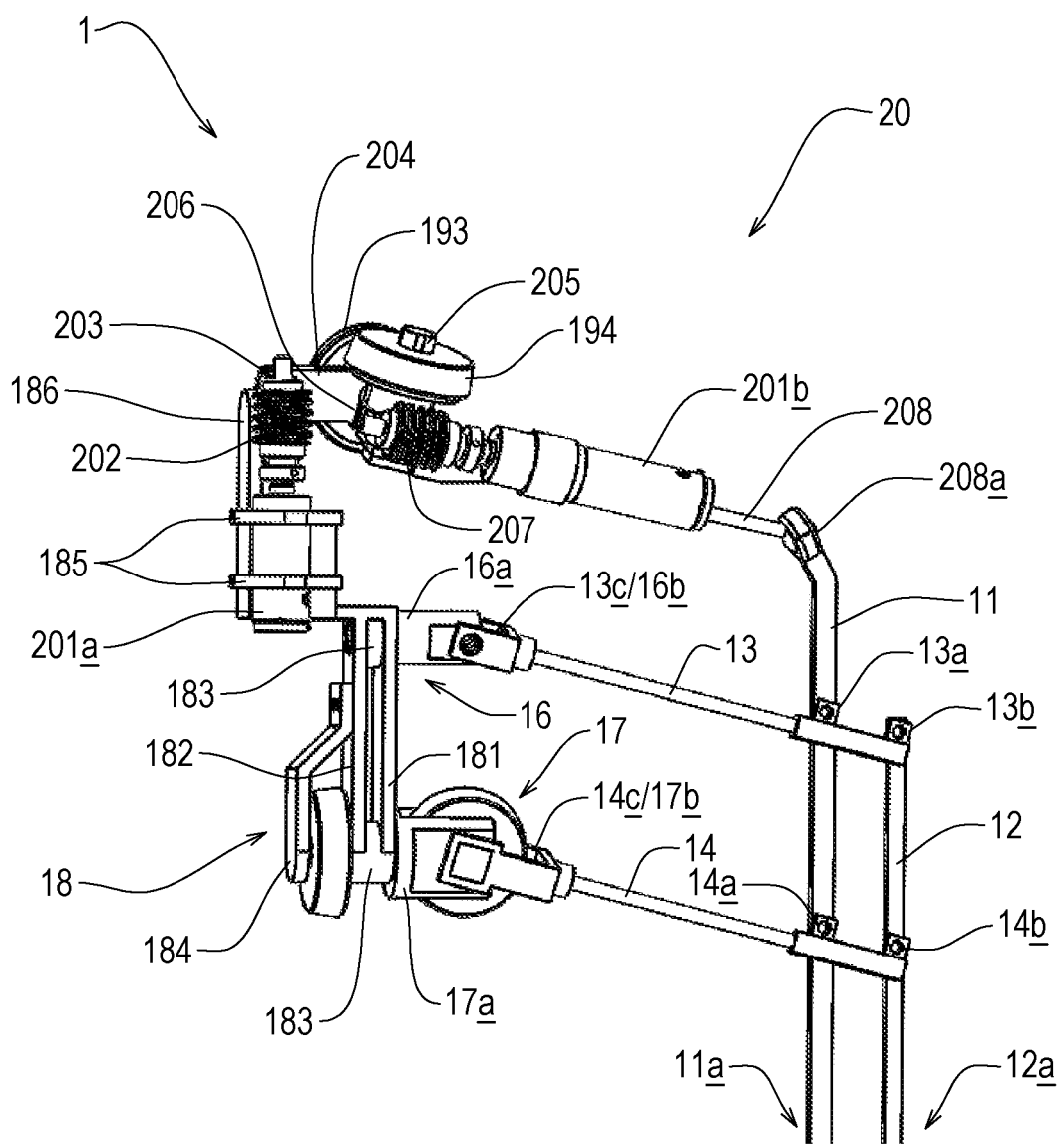

The change of mode operation continues as depicted in FIG. 5 and is generally complete in FIG. 6.

Figure 7:
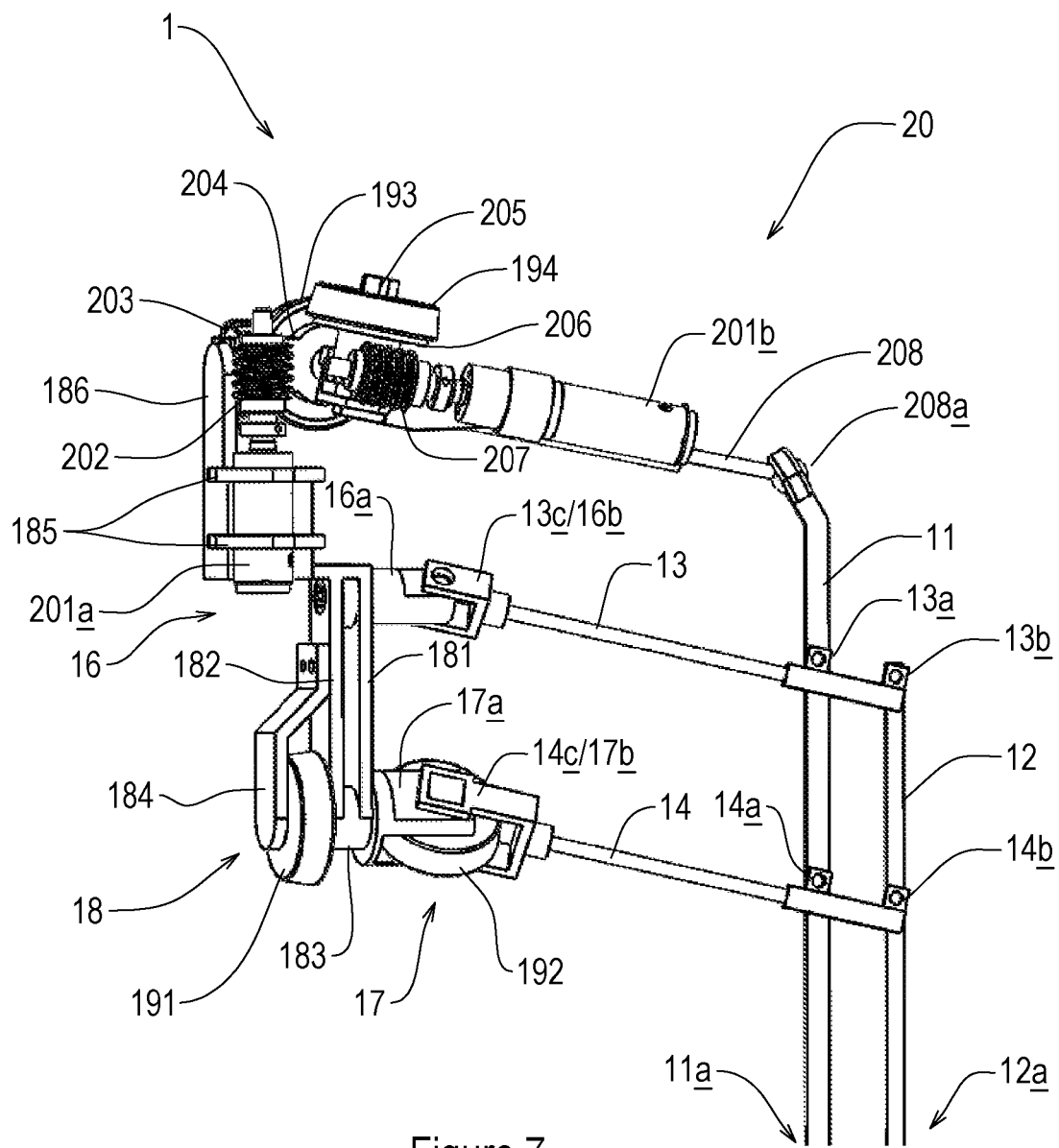
Figure 8:
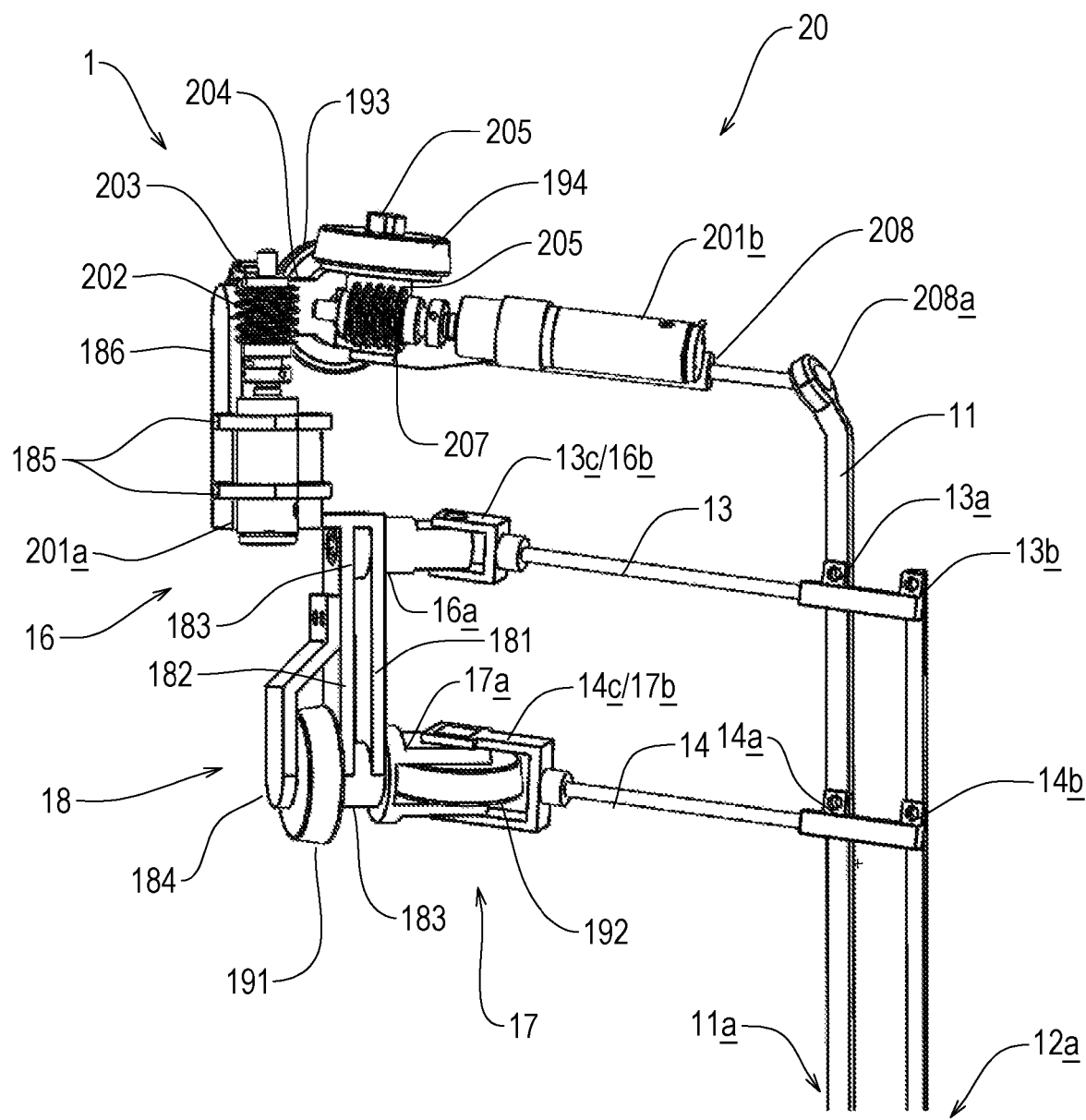

In FIG. 7, a pan operation is commenced and the second motor 201*b* is driven to cause rotation of the slide mechanism 208 about that axis. As can be seen from a comparison of FIGS. 7 and 8, the pan operation moves the first and second beam members 11,12 in a clockwise direction in this particular depicted movement. Again, as can be seen, the first and second brake elements 191,192 are in their unbraked condition during this operation—note the rotation, for example, of the first and second linkage members 14,15 about the first and second joint mechanisms 16,17.

Figure 9:
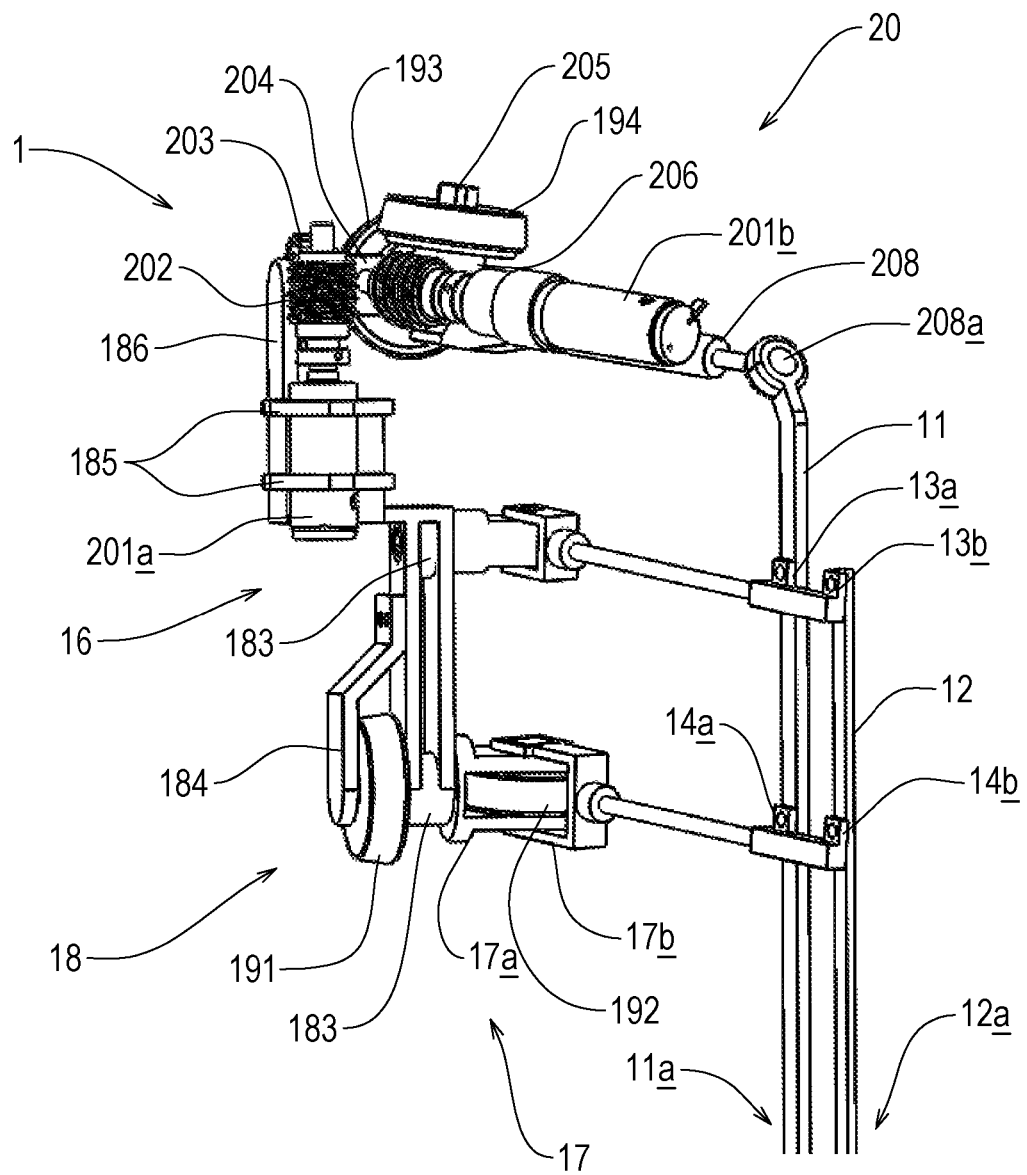

The movement is continued to the position shown in FIG. 9.

Figure 10:
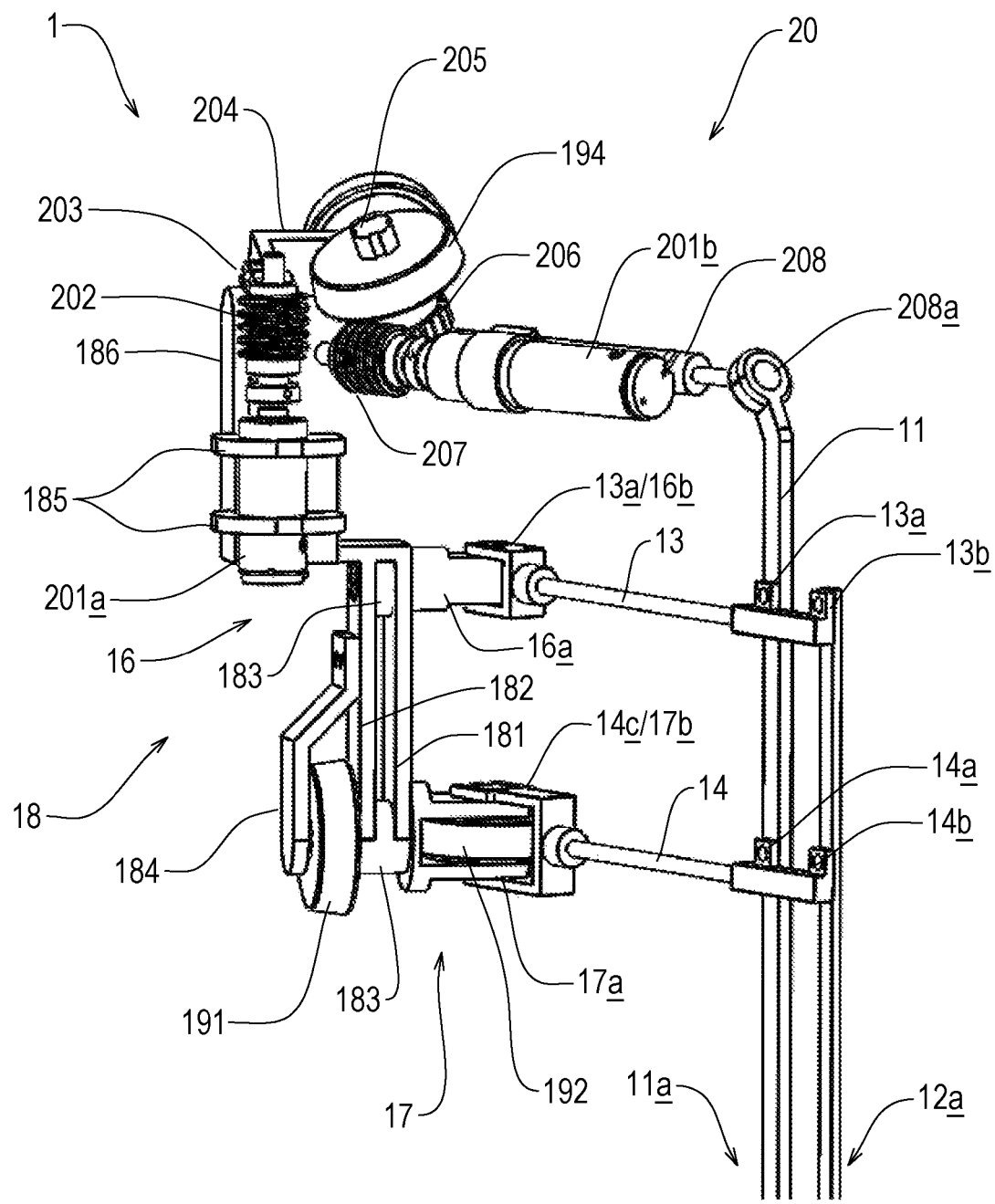
Figure 11:
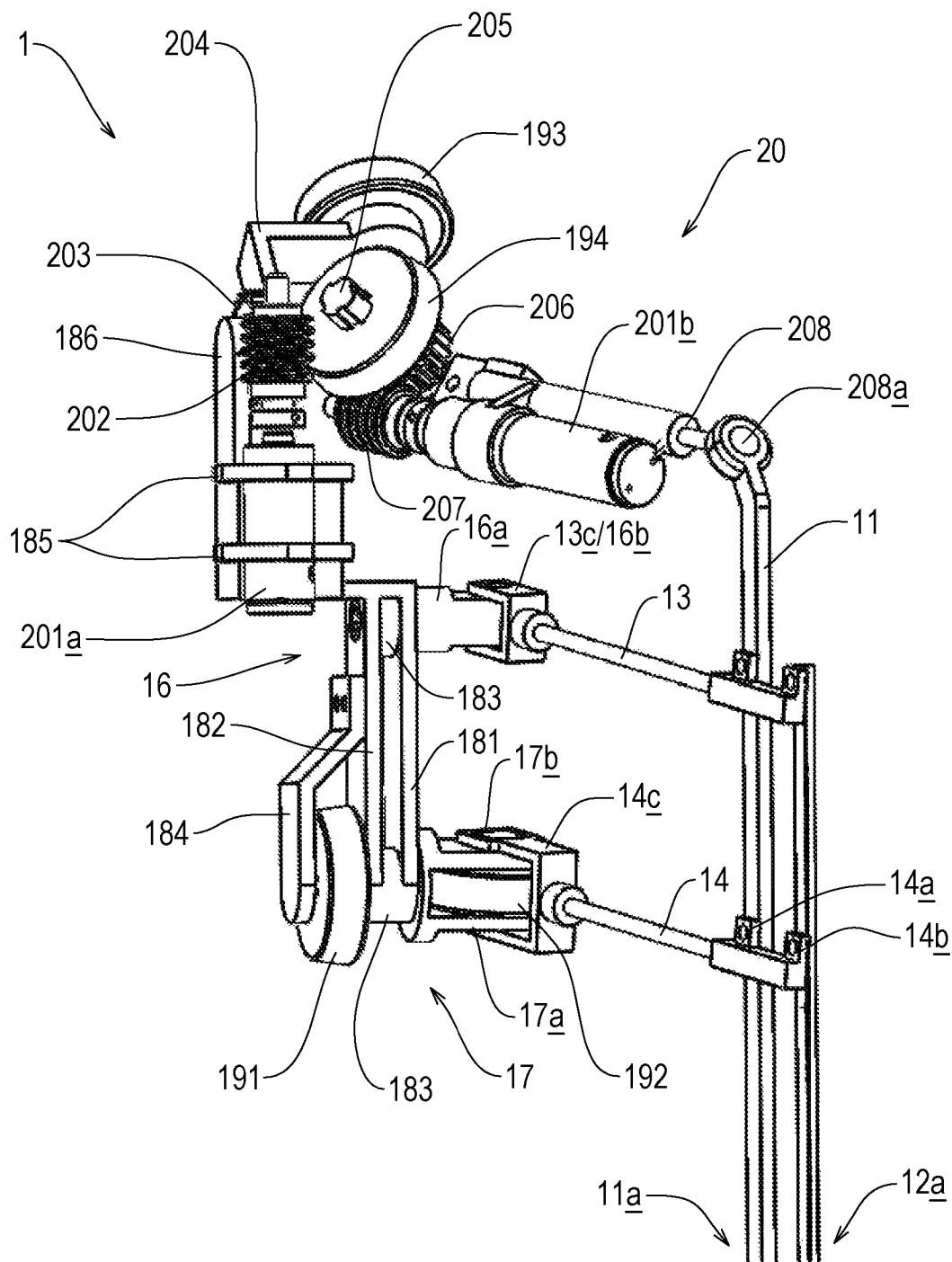
Figure 12:
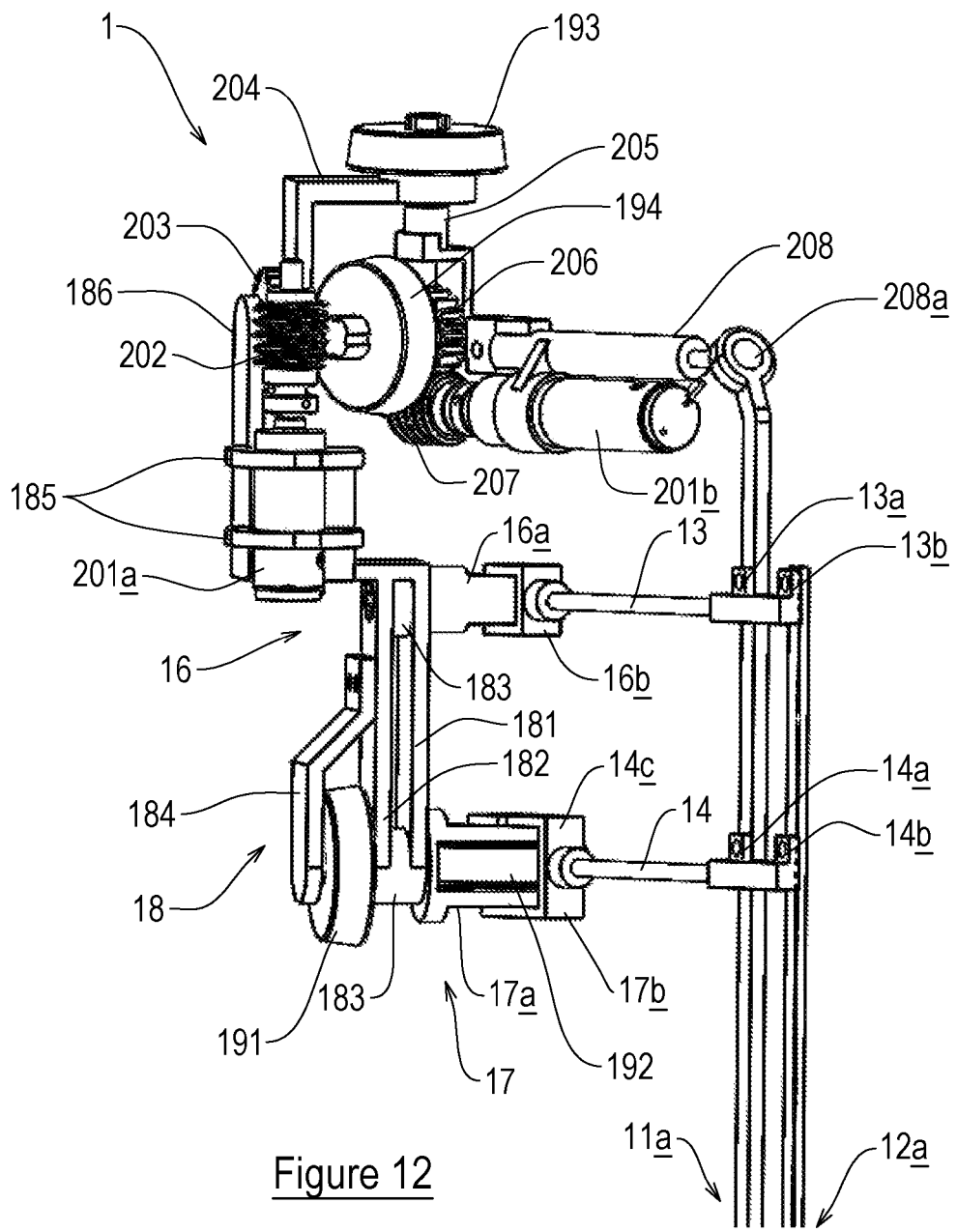

FIGS. 10-12, then depict another mode change operation from the pan to the tile mode of operation—by use of the first motor 201*a* to re-orient the second carriage axis with respect to the frame 18 (with the first and second brake elements 191,192 in their locked condition).

Figure 13:
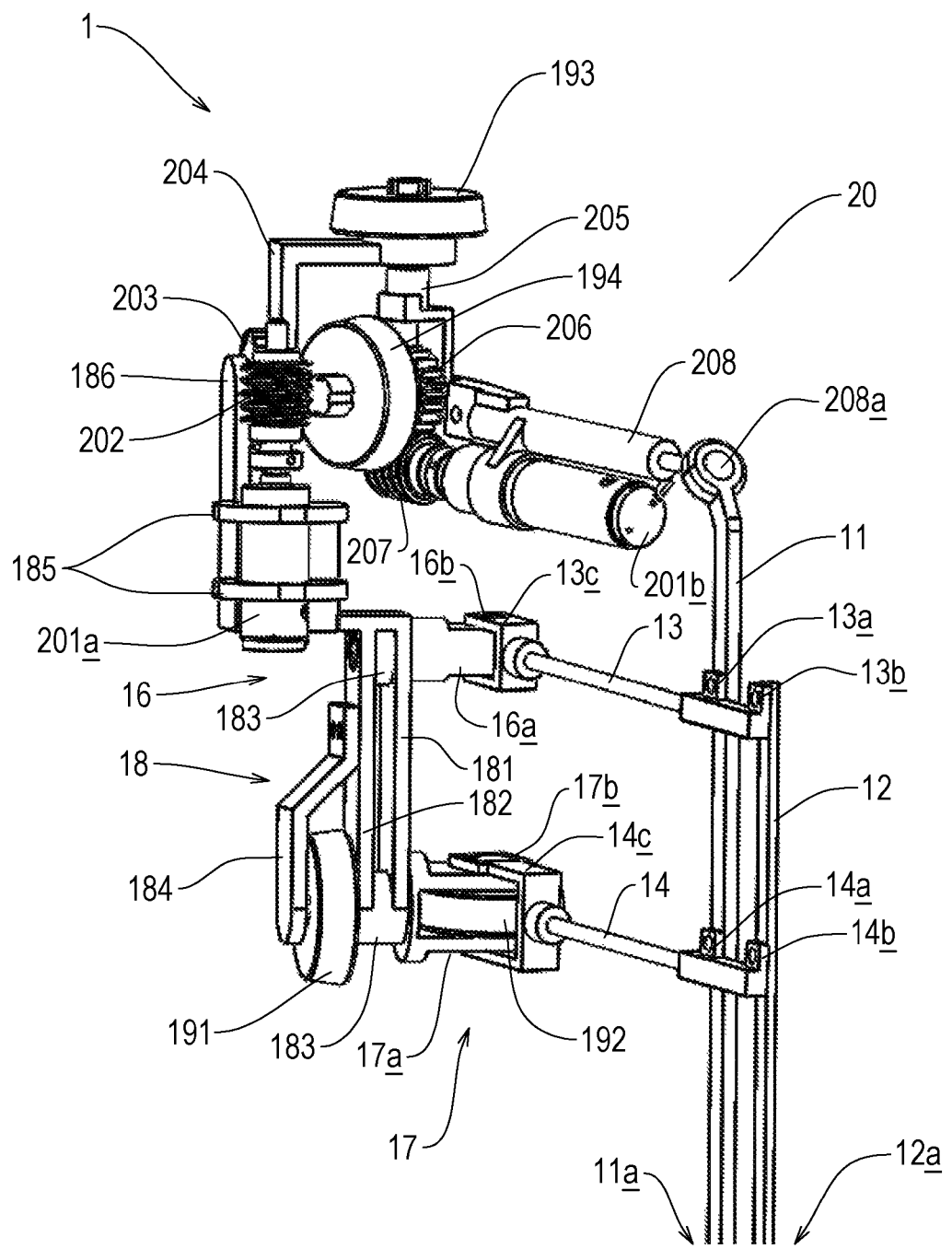
Figure 14:
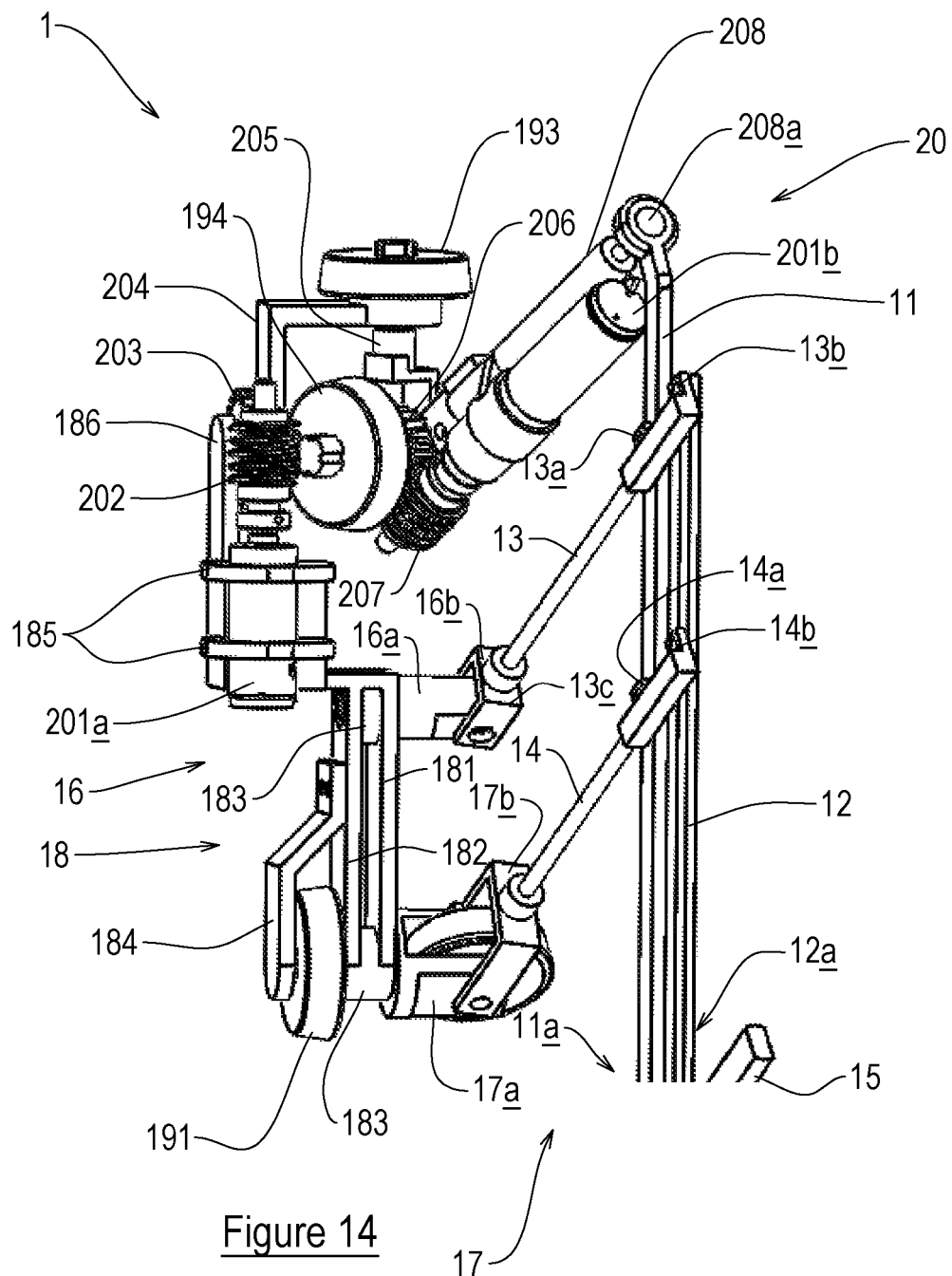
Figure 15:
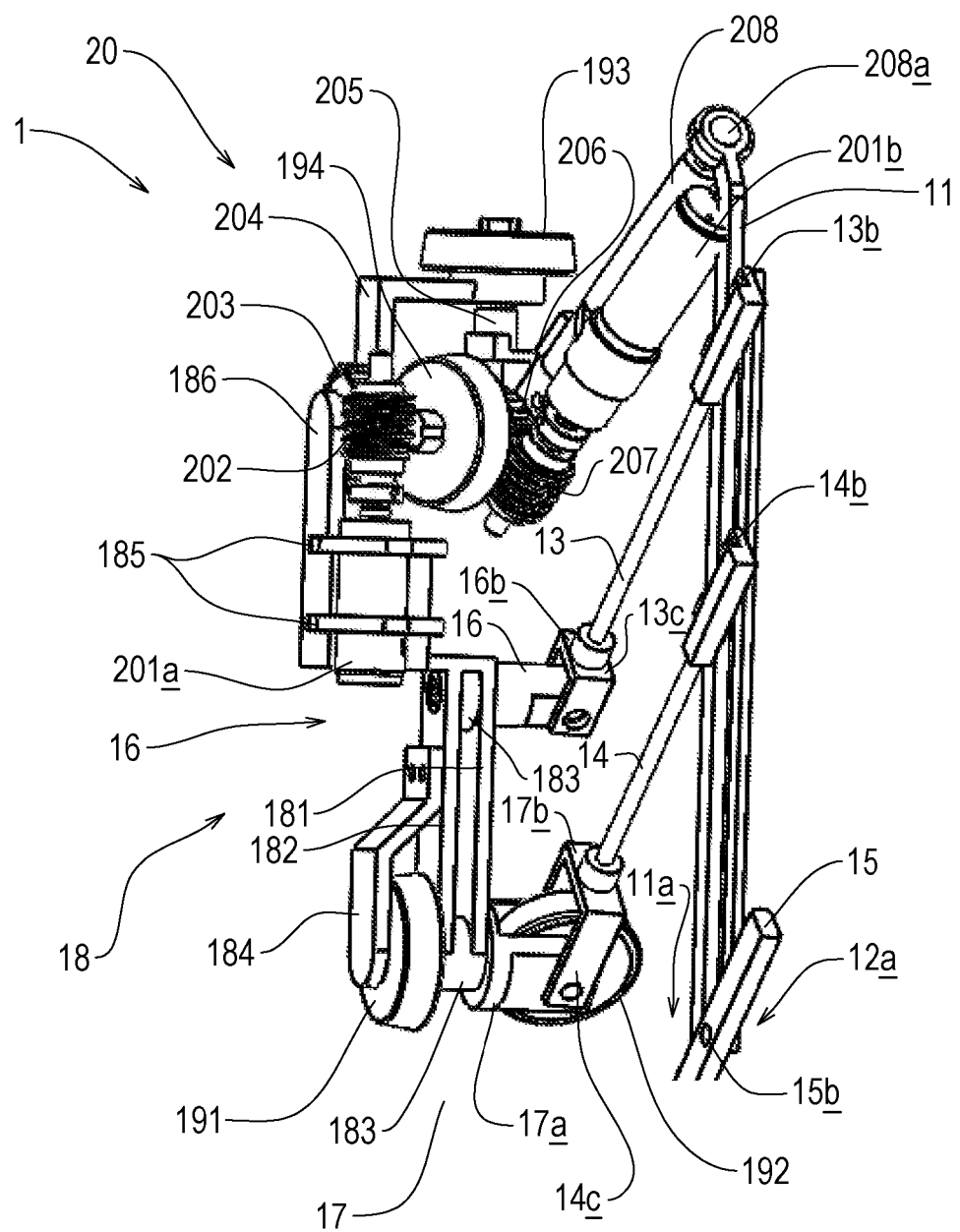

FIGS. 13-15 show a further tilt operation in which the first and second beam members 11,12 are moved generally in an anticlockwise direction.

Figure 16:
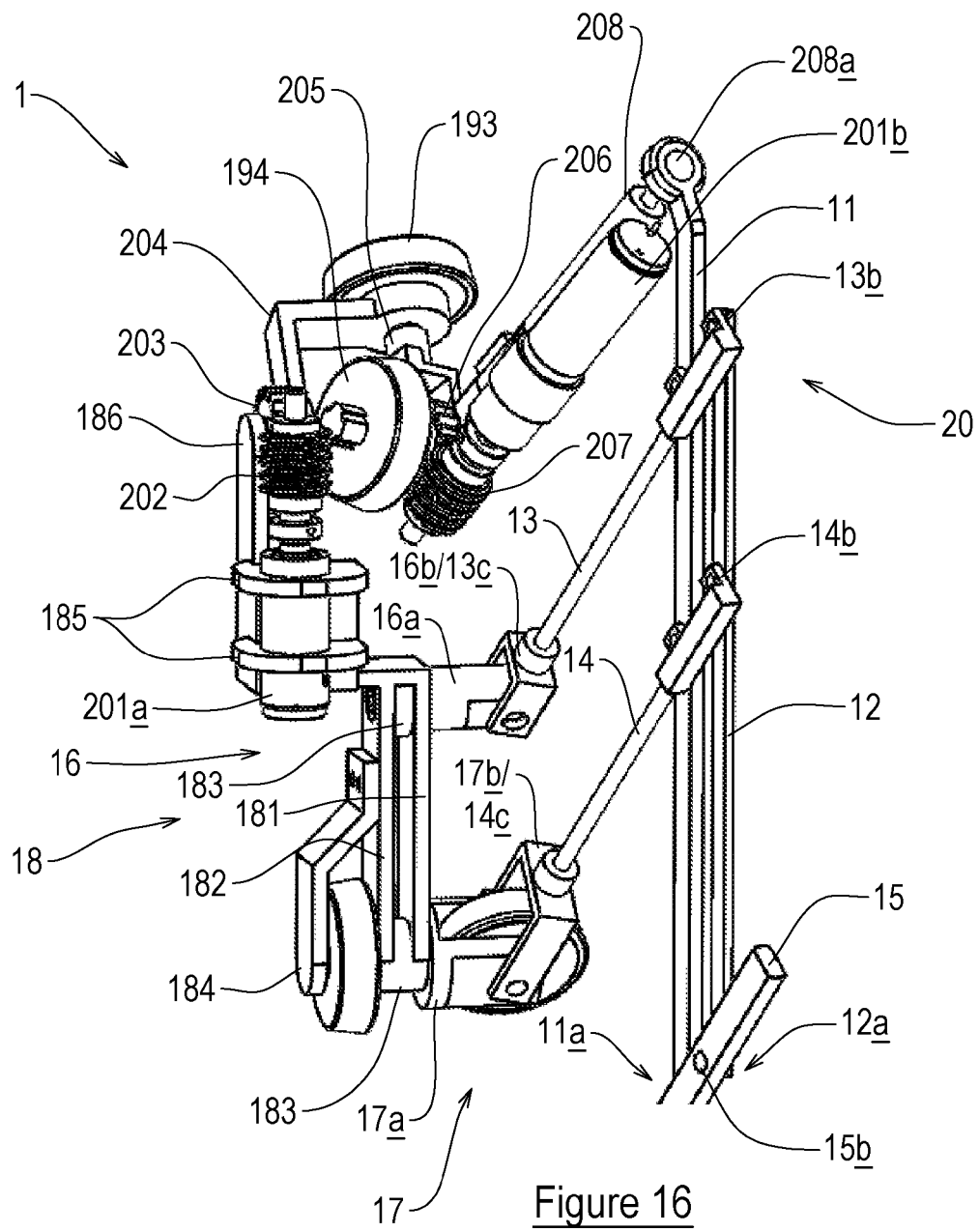
Figure 17:
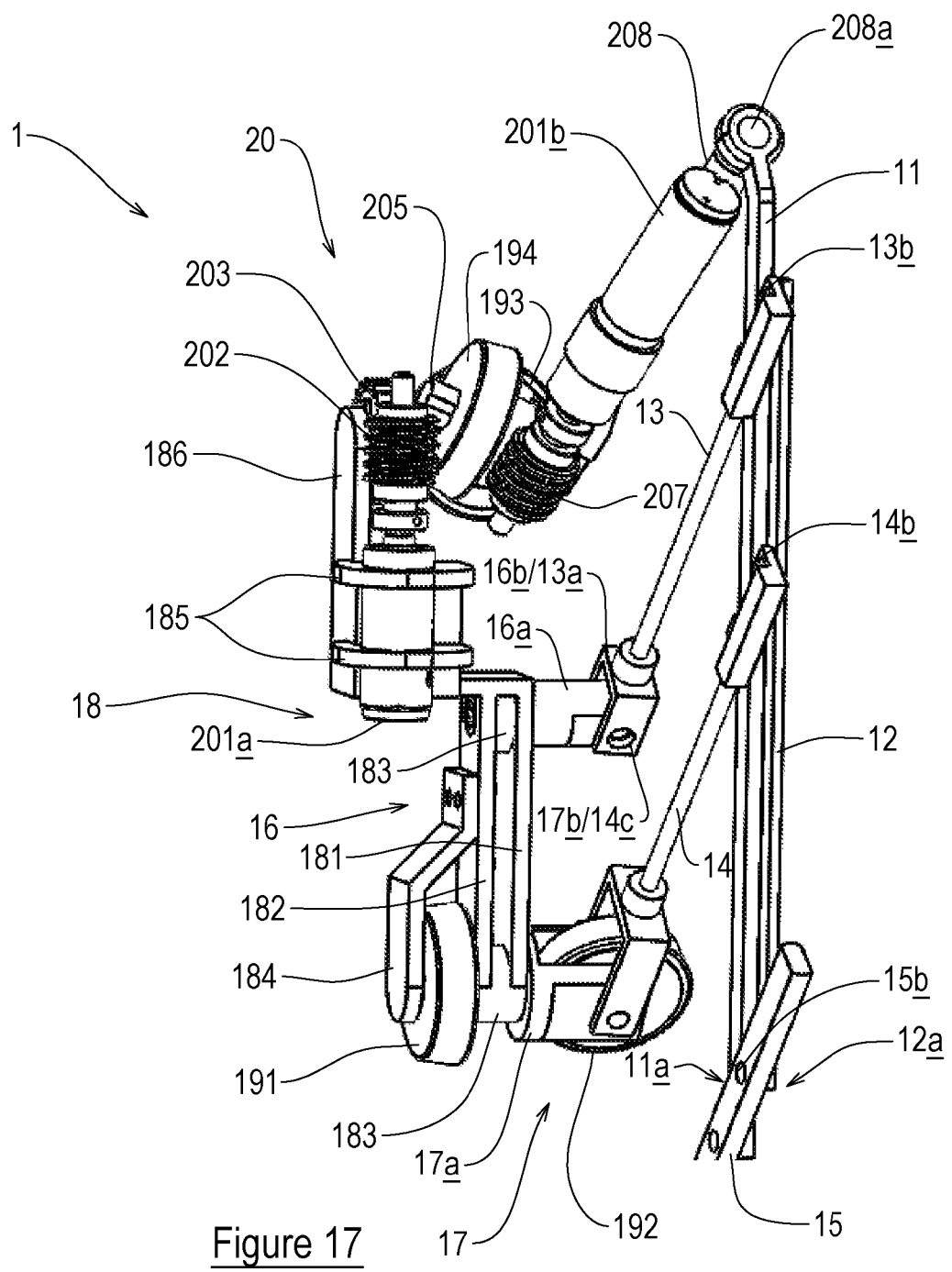

FIGS. 16-17 show a change of mode operation from the tilt mode to the pan mode.

Figure 18:
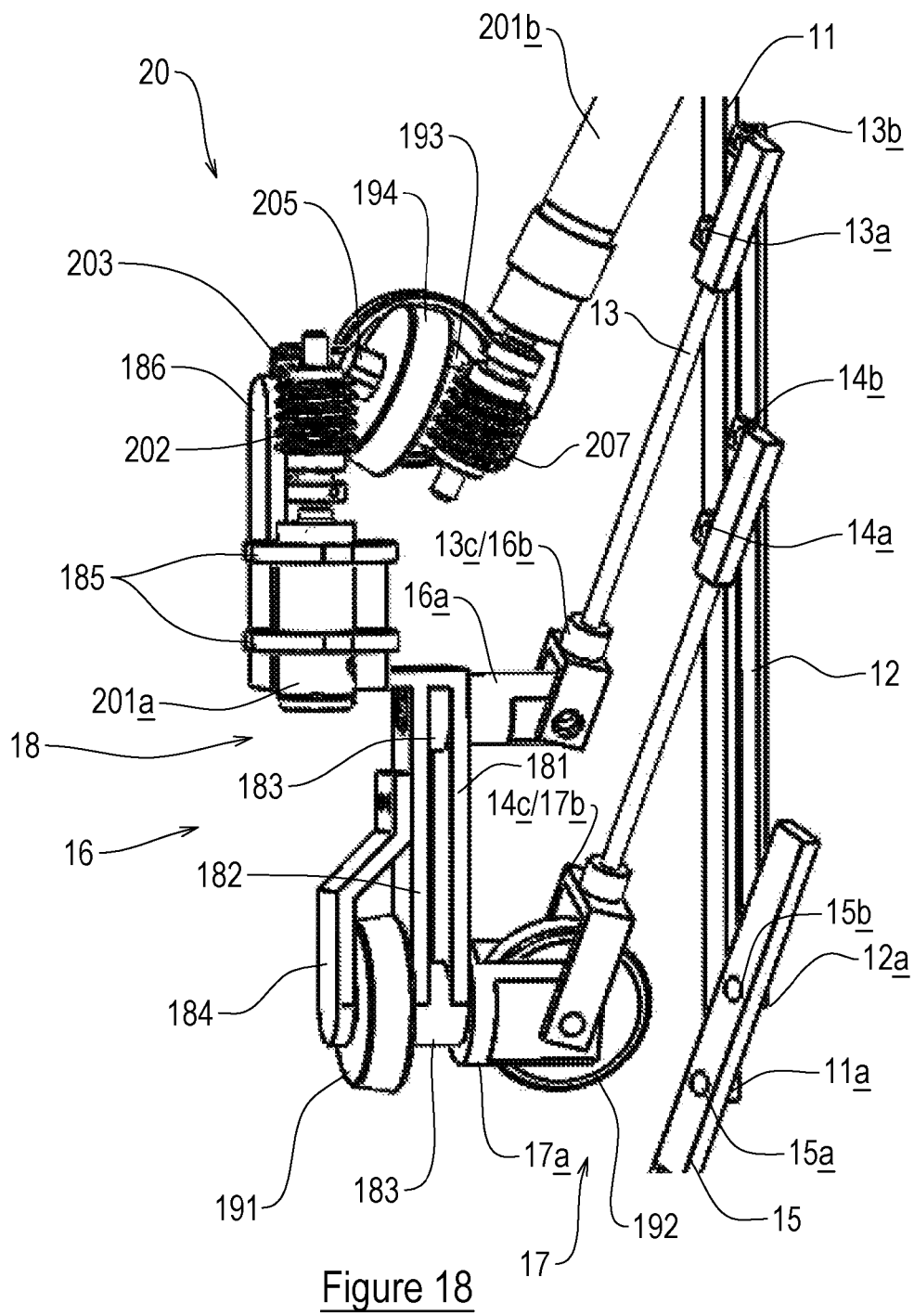
Figure 19:
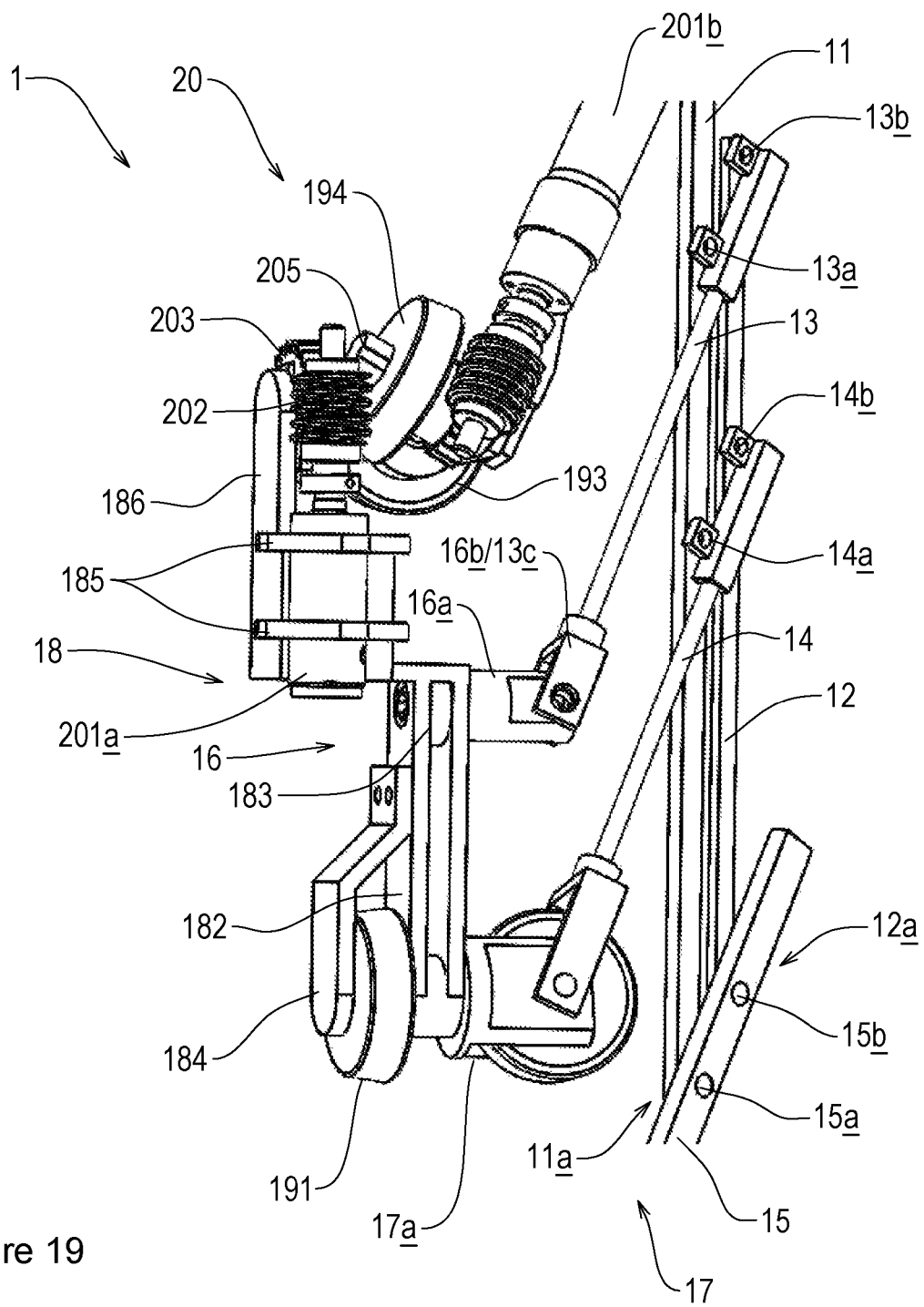

FIGS. 18-19 show a further pan operation. These figures also clearly show how the second carriage axis is oriented differently in this relatively steep tilt angle condition—compared to in the aforementioned pan operations.

The provision of first and second beam members 11,12 means that the bulk of the surgical assistant 1 (i.e. the frame 18, brake elements 19, and motors 20) can be provided relatively remotely with respect to the patient. This improves access to the patient and reduces the risks of obstructions—e.g. in the movement of equipment between surgical staff and/or so-called port clashes.

The slide mechanism 208 is used in some embodiments because the distance between the second carriage axis and the point at which the slide mechanism 208 is coupled to the beam member 11,12 changes during operation.

To perform the aforementioned operations, the control unit 103 may include and/or have access to a computer readable medium 103*b* carrying instructions to cause the operations as described herein when executed by a processor 103*c* (which may also be part of the control unit 103).

In some embodiments, the first and second beam members 11,12 may be close to one or more other parts of the surgical assistant 1, particularly when there are close to the frame 18. In such embodiments, the first and/or second beam members 11,12 may include one or more arcuate, curved, or otherwise recessed portions—configured to accommodate at least part of the one or more other parts of the surgical assistant 1. Some such embodiments are depicted, for example, in FIGS. 20, 21, and 24-37.

In some embodiments, again with FIGS. 20, 21, and 24-37 being examples, the mounting configuration 15 may be carried by first and second beam members 11,12 of the surgical assistant, wherein the axis about which pan is performed does not change orientation with respect thereto.

Figure 25:
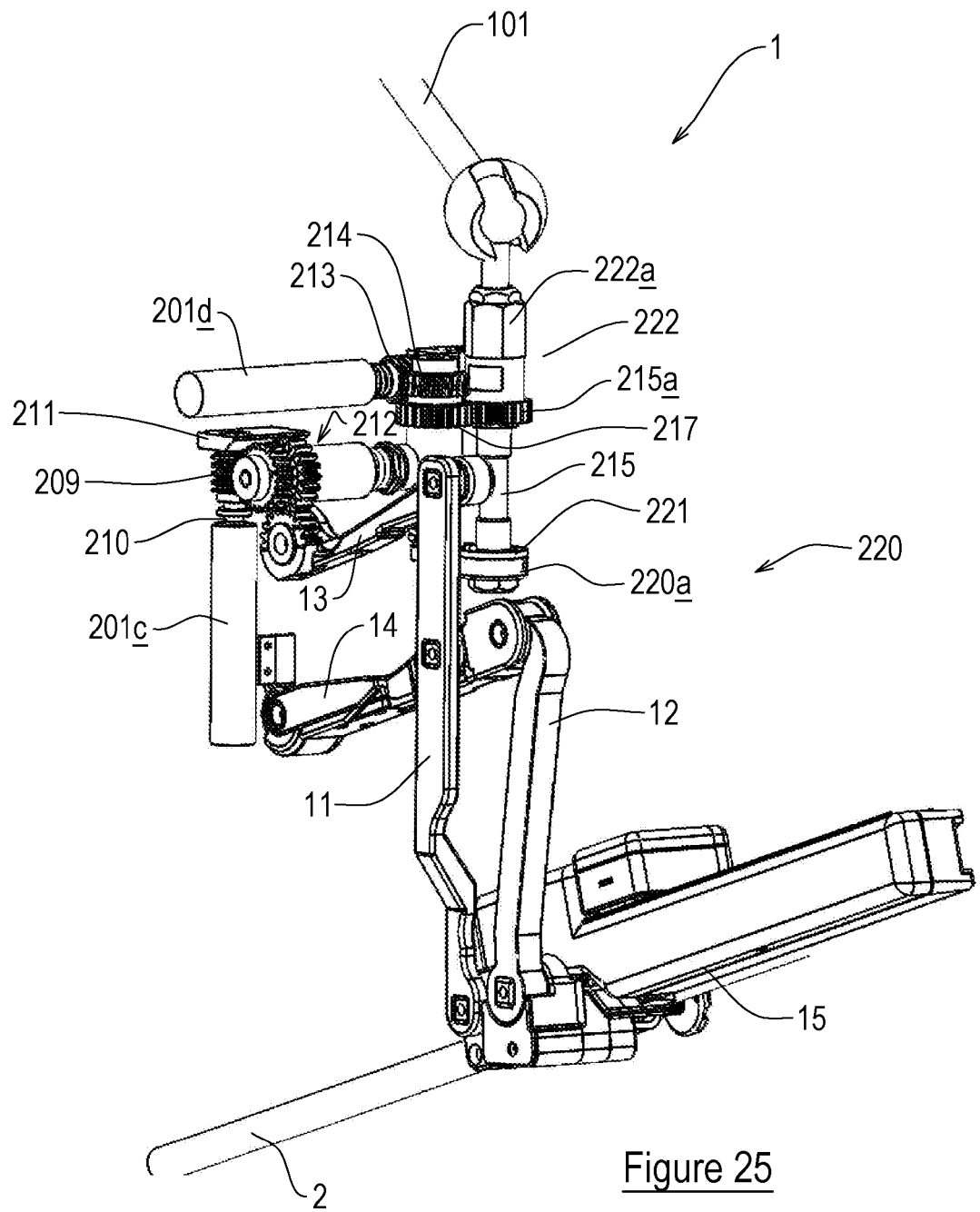
FIGS. 25 and 26 show en embodiment with a frame and housing omitted.
Figure 26:
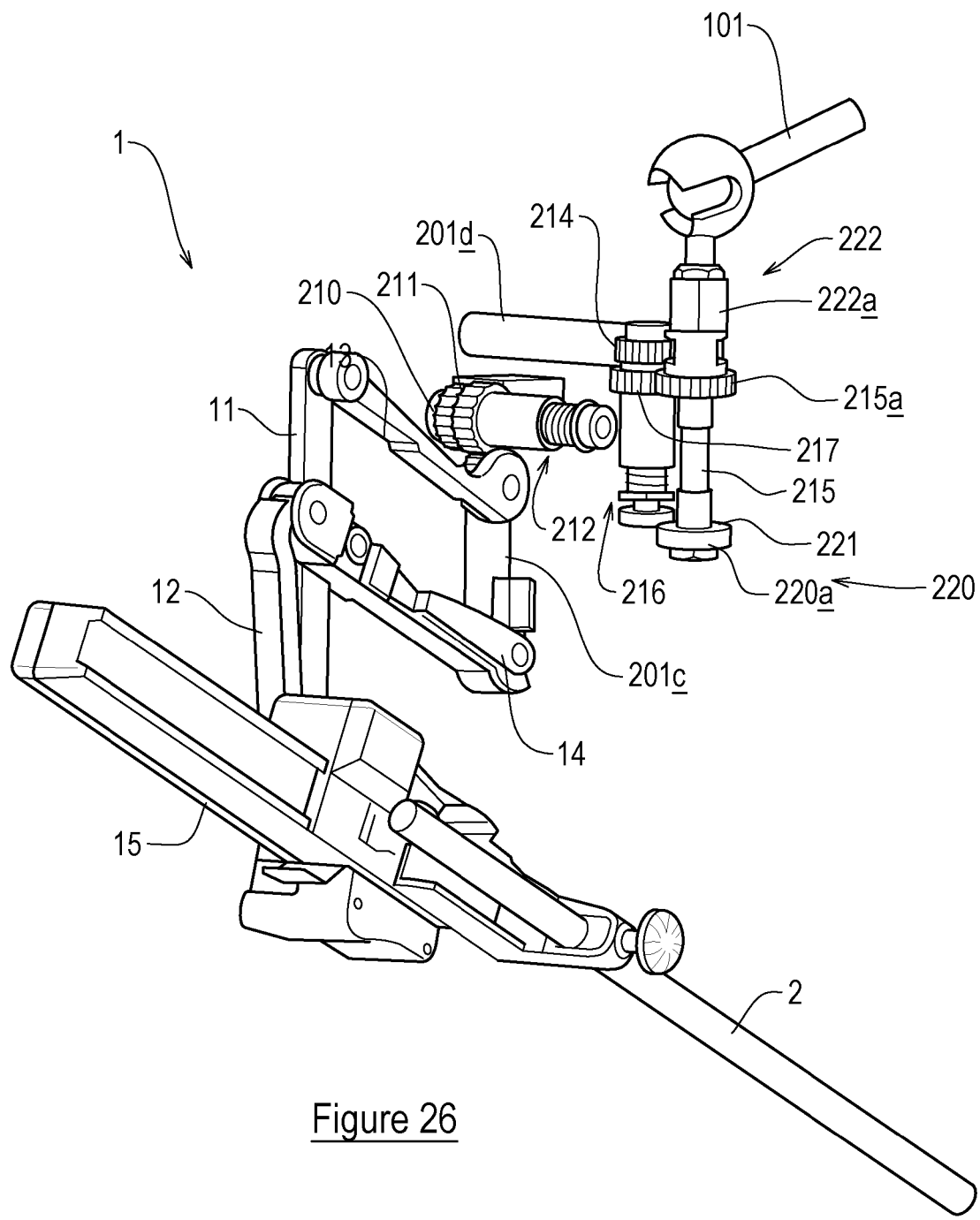
Figure 27:
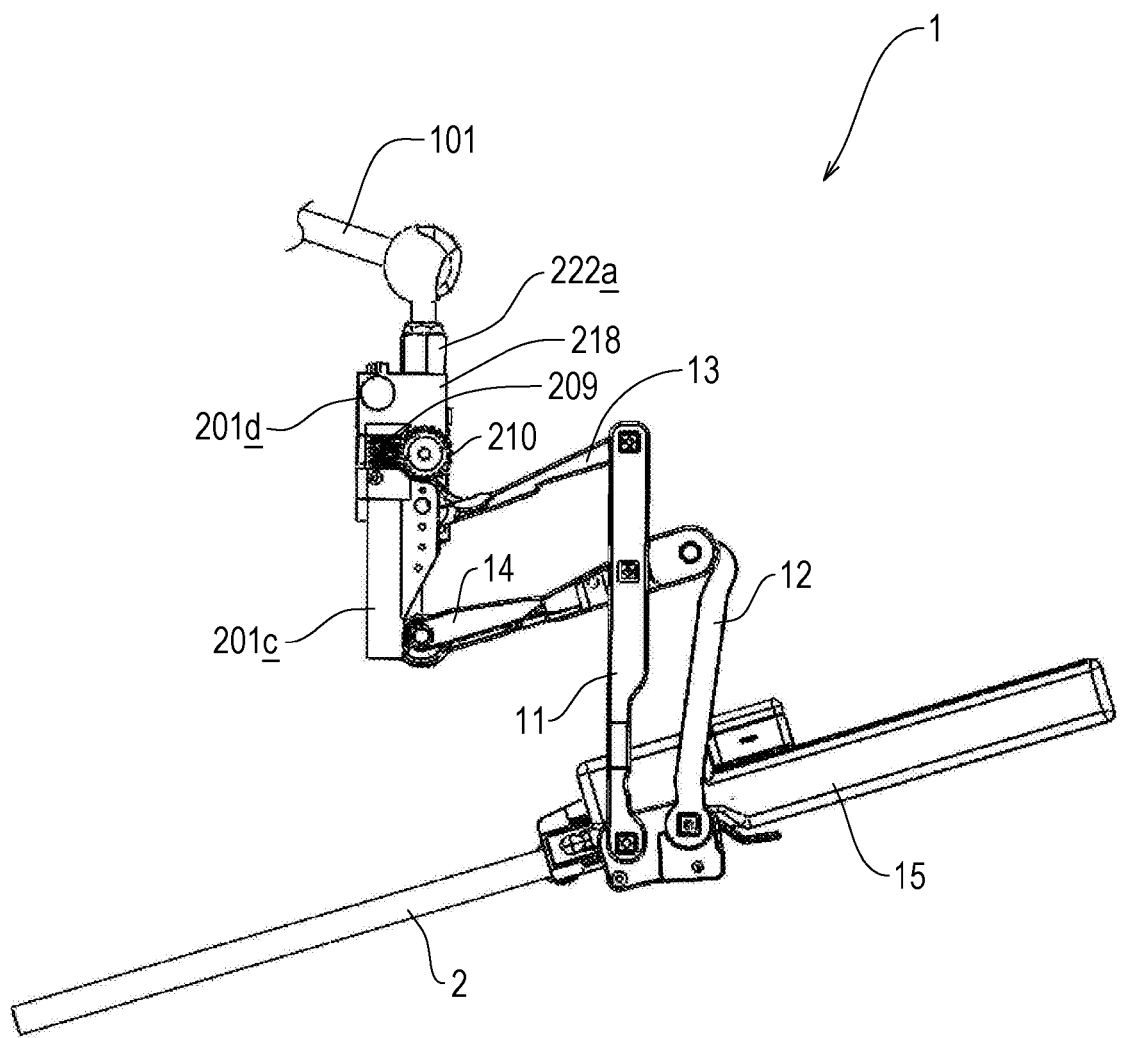
FIG. 27 shows an embodiment with the frame shown.

FIGS. 20, 21, 24, 27, 28, 29, and 30 show embodiments including a frame 18 but not including a housing 4—which would otherwise cover at least part of the frame 18. FIGS. 25 and 26 do not show the frame 18 or housing 4, to aid understanding.

In some such embodiments, first and second linkage members 13,14 may be provided to form a parallelogram arrangement. At a proximal end of one of the first and second linkage member 13,14 may be a gear which is fixed for movement with that linkage member 13,14. In such some such embodiments, the yokes 13c,14c may not be provided and the proximal ends of the two linkage members 13,14 may be coupled for rotation with respect to the frame 18 about respective axes (which are parallel to each other). In some embodiments, they are so coupled for rotation about a single respective axis each.

The frame 18 may carry a motor 20, which is generally referred to as a third motor 201c to distinguish from the first and second motors 201a,b described above. The third motor 201c may be configured to drive rotation of a third worm screw 209 (again to distinguish from the first and second worm screws 202,207 above). The third motor 201c may be oriented such that the rotor of the motor 201c is generally parallel with the first and second beam members 11,12. The third worm screw 209 may be configured to mesh with a third worm wheel 210 which may form part of a first gearbox. One or more further gears of the first gear box may mechanically couple a first drive gear 211 to the third worm wheel 210. Accordingly, rotation of the third worm wheel 210 may, through the first gearbox, drive rotation of the first drive gear 211. The first drive gear 211 may be configured to mesh with the gear of the first or second linkage member 11,12. Accordingly, the third motor 201c may be configured to drive rotation of the linkage members 13,14 with respect to the frame 18.

A clutch mechanism 212 may be provided between the drive gear 211 and the first gearbox, and/or between the drive gear 211 and the third worm wheel 210, which is configured to decouple the mechanical movement output by the first gearbox and/or the third worm wheel 210 from the drive gear 211—e.g. to allow slip between the two. This clutch mechanism 212 may be provided by a resilient biasing member which biases a side of the drive gear 211 into engagement with a rotatable output surface of the first gearbox (e.g. the side of another gear such as the third worm wheel 210, directly or indirectly)—rotation of that surface being drivable by the third motor 201c. Accordingly, by setting the biasing force applied by the resilient biasing force, the third worm wheel 210 and first drive gear 211 can be decoupled from each other (such that one is allowed to slip rotationally with respect to the other) when a force above a threshold set by the biasing force is exceeded.

According, a tilt operation may be provided.

A pan operation may be provided by a fourth motor 201d which is mounted to cause rotation of the frame 18 about a pan axis. The fourth motor 201d may be mounted such that a rotor thereof extends generally perpendicularly with respect to the rotor of the third motor 201c. The fourth motor 201d may be located at or towards one end of the third motor 201c, with the two motors 201d,c generally extending perpendicular to each other. In some embodiments, the fourth motor 201d is supported by the frame 18 at a part of the frame 18 which is generally remote from the arm 101. In some embodiments, the fourth motor 201d is supported by the frame 18 at a part of the frame 19 which is generally adjacent or proximal to the arm 101.

The rotor of the fourth motor 201d may carry a fourth worm screw 213 which is configured to mesh with a fourth worm wheel 214. Rotation of the fourth worm wheel 213 may cause rotation of the frame 18 about a mounting shaft 215 (which may be a "pan" shaft because movement around that shaft may be viewed as a pan movement).

Accordingly, the fourth worm wheel 214 may be mounted to the mounting shaft 215 for rotation therewith.

In some embodiments, however, the fourth worm wheel 214 is coupled to the mounting shaft 215 via a second gearbox of which the fourth worm wheel 214 may form a part in some embodiments. The second gearbox may include a second drive gear 217 which is configured to mesh with a mounting shaft gear 215a. The mounting shaft gear 215a may be configured for rotation with the mounting shaft 215. In some embodiments, the second drive gear 217 is configured to be driven by the fourth worm wheel 214 and is, therefore, coupled thereto.

Accordingly, the coupling of the fourth worm wheel 214 to the second drive gear 217 (and/or the second gearbox) may be through a further clutch mechanism 216—although reference to this as a "further" clutch mechanism does not mean that the clutch mechanism 212 has to be provided in all embodiments including the "further" clutch mechanism 216).

The further clutch mechanism 216 may be provided by a resilient biasing member which biases a side of the second drive gear 217 into engagement with a rotatable surface of the second gearbox (e.g. the side of another gear such as the fourth worm wheel 214, directly or indirectly)—rotation of that surface being drivable by the fourth motor 201d. Accordingly, by setting the biasing force applied by the resilient biasing force, the fourth worm wheel 214 and second drive gear 217 can be decoupled from each other (such that one is allowed to slip rotationally with respect to the other) when a force above a threshold set by the biasing force is exceeded.

As such, a pan operation may be provided.

The third and fourth motors 201c,d and/or first and second gearboxes may be provided generally so that are within a common plane (or common planes). This enables a relatively thin frame 18 to be provided in some embodiments.

The frame 18, and/or the third and fourth motors 201c,d, and/or the first and second gearboxes may be provided in a housing 4 which extends generally radially from the mounting shaft 215 in the same radial direction. This then allows for a relatively large degree of rotational freedom about the mounting shaft 215.

However, 360 degrees of rotational movement of the frame 18 about the mounting shaft 215 may not be desirable or possible in some embodiments.

In some embodiments, a total rotation of more than 360 degrees may be provided such that the frame 18 can rotate more than 180 degrees in both a clockwise and an anticlockwise direction about the mounting shaft 215 with respect to a predetermined rotational position about the mounting shaft 215. This rotation may be more than 200 degrees in each of two opposing directions from a predetermined rotational position about the mounting shaft 215. The rotation may be 225 degrees in each direction. The total range of pan movement may, therefore, be more than 360 degrees and may be 450 degrees.

Accordingly, a stop mechanism 220 may be provided—see FIGS. 24 and 29-33.

The stop mechanism 220 may include a first stop member 220a and a second stop member 220b. The first stop member 220a and second stop member 220b may be configured to engage each other for rotational movement with respect to each other through a permitted range of movement (the permitted range being greater than 360 degrees around an axis of the stop mechanism 220).

Accordingly the first stop member 220a may be mounted for rotation with the mounting shaft 215 and the second stop member 220b may be mounted for rotation with the frame 18.

In some embodiments, the first stop member 220a may be located at a distal end of the mounting shaft 215 which may be remote from a proximal end thereof (which may be secured to the arm 101, for example, by a ball joint). The distal end of the mounting shaft 215 may carry a head member which includes two or more surfaces which are each configured to fit at least partially within and engage the first stop member 220a. Accordingly, in some embodiments, the first stop member 220a defines a recess which is configured to receive at least part of the head member of the mounting shaft 215—this may secure the first stop member 220a against rotation with respect to the mounting shaft 215. The mounting shaft 215 may further pass through an aperture of the first stop member 220a—such that, in some embodiments, the first stop member 220a is generally for an annular shape with a central aperture configured to receive at least part of the mounting shaft 215.

The mounting shaft 215 may pass through an aperture defined by the frame 18 and/or housing 4, such that the first stop member 220a is generally adjacent the frame 18 and/or housing 4. Accordingly, the second stop member 220b may be located at this point such that the second stop member 220b sits between the head member of the mounting shaft 215 and the frame 18 and/or housing 4.

The engagement of the first stop member 220a and the second stop member 220b may be an indirect mounting such that, for example, a third stop member 221 of the stop mechanism 220 is provided between the first and second stop member 220a,b.

The third stop member 221 may be a floating member in that it is generally free for rotation with respect to both the first (through a first range of motion) and the second (through a second range of motion) stop members 220a,b—to provide a combined limited range of motion of the frame 18 with respect to the mounting shaft 215. The first and second ranges of motion may be limited ranges of less than 360 degrees each but which combine to provide a larger range of motion for the frame 18 with respect to the mounting shaft 215.

In some embodiments, the third stop member 221 includes protrusions 221a,b. A first of these protrusions 221a may be configured to be at least partially received by the first stop member 220a and a second of these protrusions 221b may be configured to be at least partially received by the second stop member 220b.

As such, the first and second protrusions 221a,b may extend from the third stop member 221 in opposing directions.

In some embodiments, the third stop member 221 also defines an aperture which is configured to receive at least part of the mounting shaft 215. The third stop member 221 may be generally annular in form.

The first stop member 220a may define a first arcuate recess 220aa which is configured to receive the at least part of the first protrusion 221a and which extends around a first arc.

The second stop member 220b may define a second arcuate recess 220ba which is configured to receive the at least part of the second protrusion 221b and which extends around a second arc.

The first and second arcs may be generally of the same degree of curvature. However, the first arc may be longer then than the second arc. The degree of curvature of the first and second arcs may generally match the curve defined by the radial position of the first and second protrusions 221a, 221b of the third stop member 221 with respect to a central axis thereof (which may be an axis of rotation of the third stop member 221 with respect to the mounting shaft 215.

Accordingly, rotation of the frame 18 and/or housing 4 with respect to the mounting shaft 215 may cause movement of the third stop member 221 with respect to the frame 18 and/or housing 4. The second protrusion 221b may reach an end of the second arcuate recess 220ba and then be prohibited from further rotation with respect to the second stop member 220b by engagement of the second protrusion 221b with a wall defining the end of the second arcuate recess 220ba. During this rotational movement, the third stop member 221 may not move or may not move substantially with respect to the first stop member 220a (although free to do so).

Further rotation of the frame 18 and/or housing 4 with respect to the mounting shaft 215 may cause rotation of the third stop member 221 with respect to the first stop member 220a until the first protrusion 221a reaches an end of the first arcuate recess 220aa and engages a wall defining an end of that recess 220aa. This may then stop further rotational movement of the frame 18 and/or housing 4 with respect to the mounting shaft 215 (i.e. further pan movement).

The second arcuate recess 220ba may be defined generally inwardly (i.e. on an inboard side) with respect to an aperture defined by the frame 18 and/or housing 4 which is configured to receive the mounting shaft 215. The second arcuate recess 220ba may be such that it does not extend between this aperture and an adjacent edge or extremity of the housing 4 and/or frame 18.

The use of this first and second arcuate recess 220aa,ba arrangement may, therefore, permit a wide rotational degree of freedom to be permitted whilst allowing the mounting shaft 215 to be located relatively close to the edge or extremity of the frame 18 and/or housing 4. In some other arrangements, providing a longer second arcuate recess 220ba (perhaps to the exclusion of the first arcuate recess 220aa and perhaps without the first and third stop members 220a,221 both being provided) would mean that more frame 18 and/or housing 4 would need to be provided around the aperture in order to provide the second arcuate recess 220ba and any consequential structural strength. In addition, in such arrangements the total movement may not be greater than 360 degrees—the three part form of the stop mechanism 220 may allow more than 360 degrees of movement in total to be provided and limited.

As will be appreciated, the use of the third stop member 221 also provides a bearing member—such that the material of the third stop member 221 and/or a coating thereof can be provided to allow for a hardwearing and low friction bearing to be provided between the mounting shaft 215 and the frame 18 and/or housing 4.

FIGS. 34 to 37 show different rotational positions about the pan axis—with the housing 4 and frame 18 at different rotational positions. In some embodiments, the frame 18 and housing 4 may rotate such that the tool 2 passes under the arm 101 or otherwise past the arm 101.

In some embodiments, the mounting shaft 215 is coupled to the arm 101, or to a joint member of the arm 101, by a coupler 222. The coupler 222 may be secured for rotation with the mounting shaft 215 and may include a threaded socket member 222a which is configured to receive and engage with a correspondingly threaded part of the arm 101 or joint member thereof.

One or more dowel pins may be used to secure one or more of the gears and/or couplers to their respective shafts for rotation therewith.

As will be understood, the pan axis may be offset from the first and second axes (of the first and second beam members 11,12). Therefore, to provide a confocal or goniometric point for the tool 2, the mounting configuration 15 may be coupled to the first and second beam members 11,12 such that a longitudinal axis of a tool 2 secured thereto intersects the pan axis. The bulk of the frame 18 and/or housing 4 may extend generally towards the first and second axes (rather than in the opposite direction), in order to allow for a greater degree of rotational pan movement.

In some embodiments described herein, the first and/or second linkage members 13,14 may be configured, when in a configuration close to each other, to interleave and/or overlap. As such, in some such embodiments, one of the linkage members 13,14 may include a recess or groove which is configured to receive at least part of the other in such configurations. Indeed, in some embodiments, one of the linkage members 13,14 may be separated into two adjacent parts separated by a gap which is configured to receive at least part of the other linkage member 13,14 in such configurations. This may allow steeper tilt angles to be achieved, for example.

In some embodiments, the first linkage member 13 may be provided substantially in a first linkage plane and the second linkage member 14 may be provided substantially in a second linkage plane (the two linkage planes being generally parallel with each other). This may allow, for example, the two linkages 13,14 to fold such that the first and second beam members 11,12 may be closer together (these beam members 11,12 may also be substantially provided in the first linkage plane and second linkage plane respectively).

Figure 28:
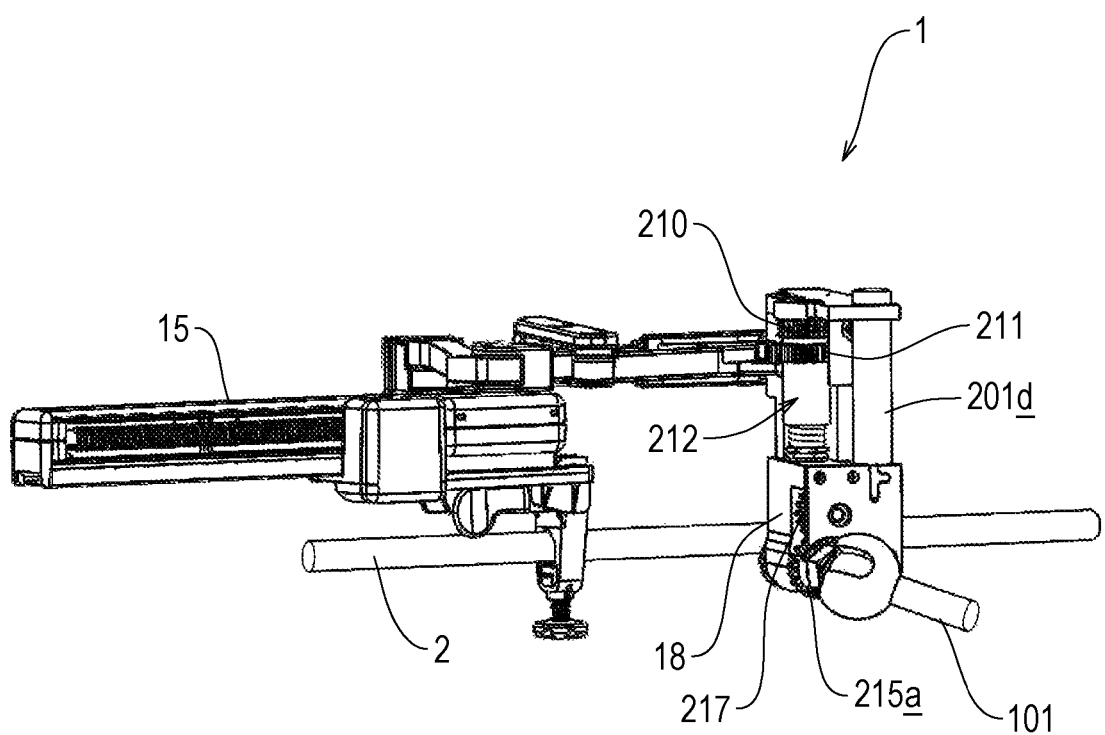
FIG. 28 shows an embodiment is a different orientation.
Figure 29:
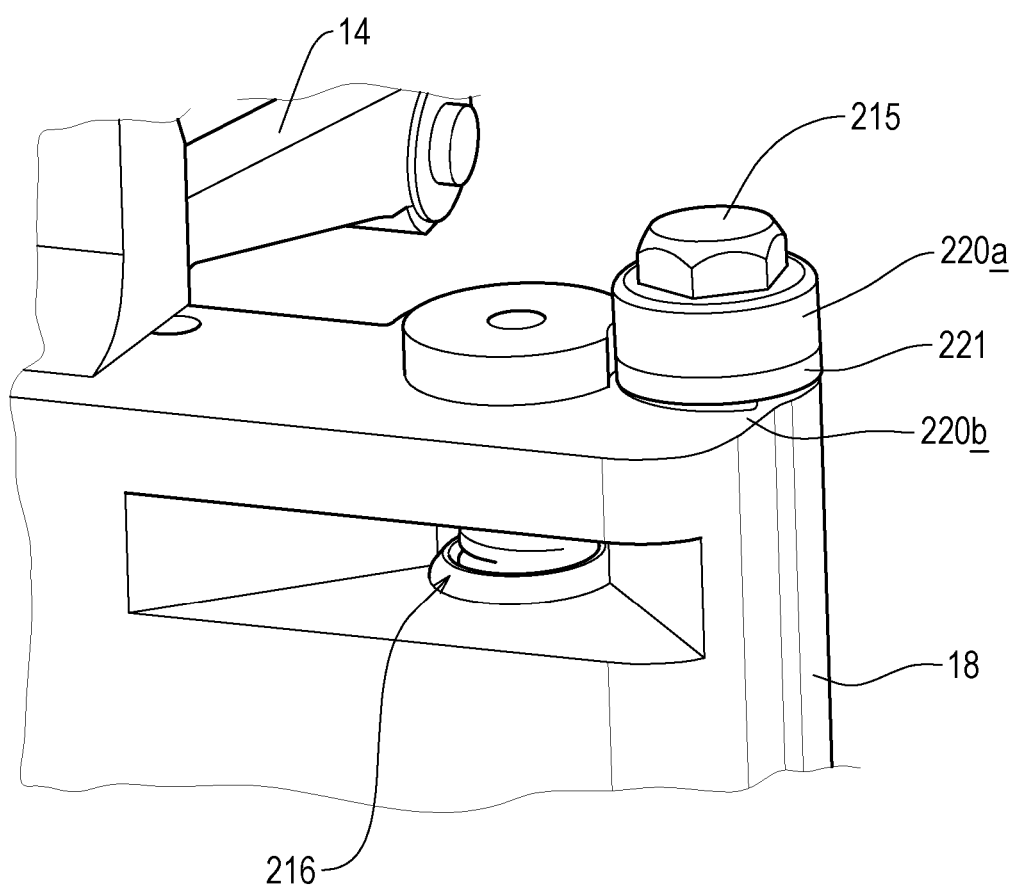
FIGS. 29-33 show a stop mechanism.
Figure 30:
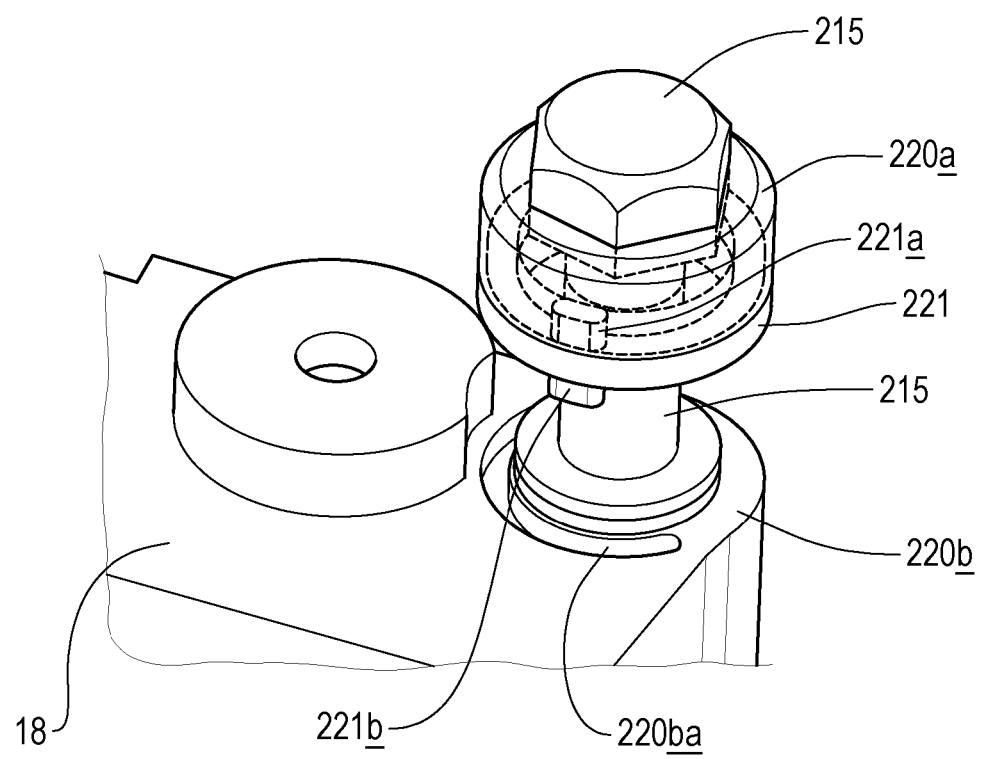
Figure 31:
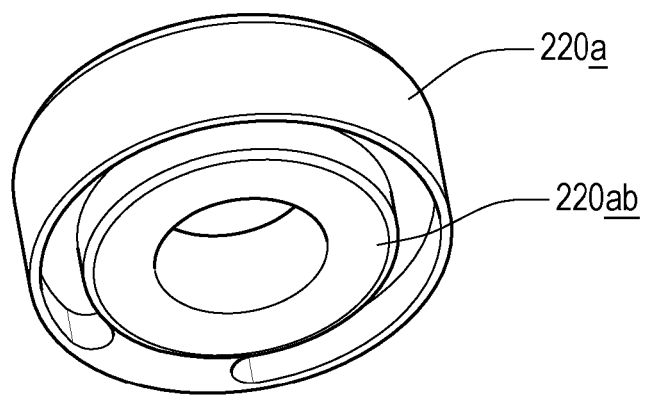
Figure 32:
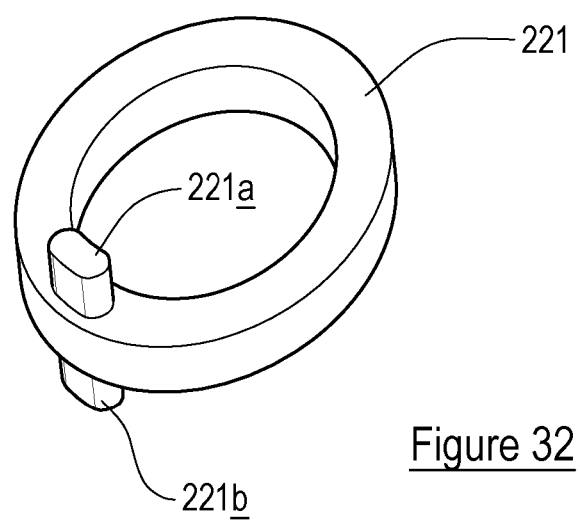
Figure 33:
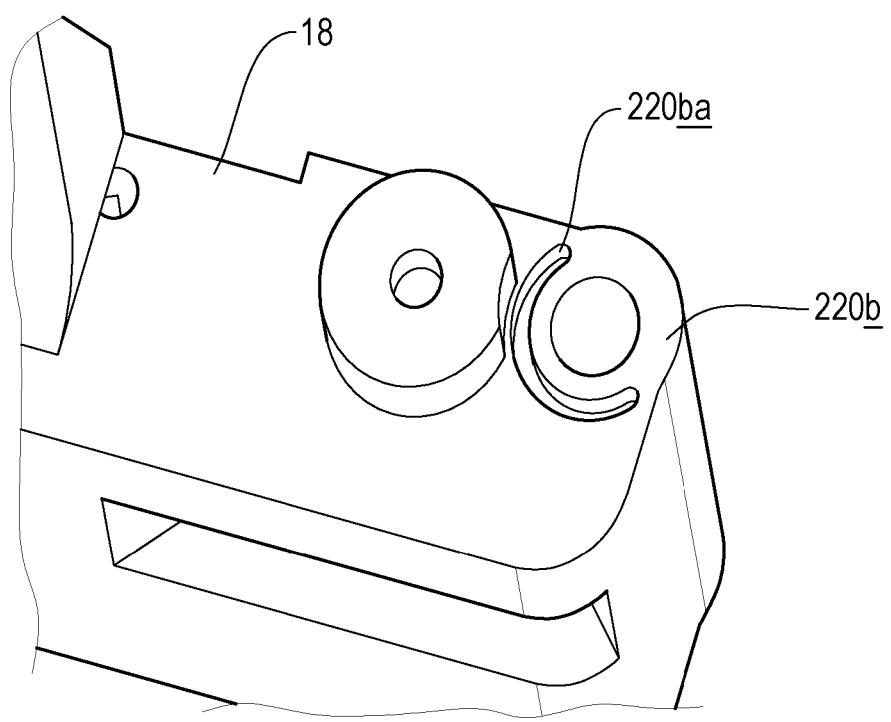
Figure 34:
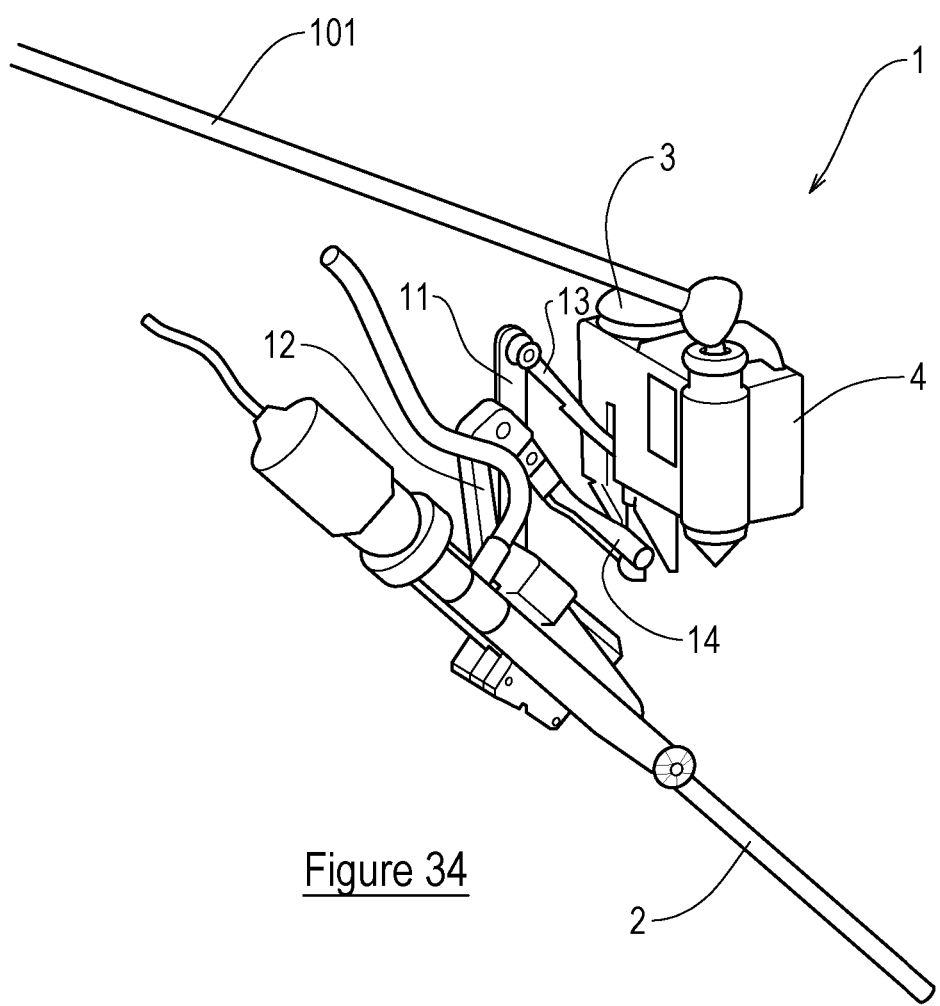
FIGS. 34-37 show an embodiment in various different pan rotational positions.
Figure 35:
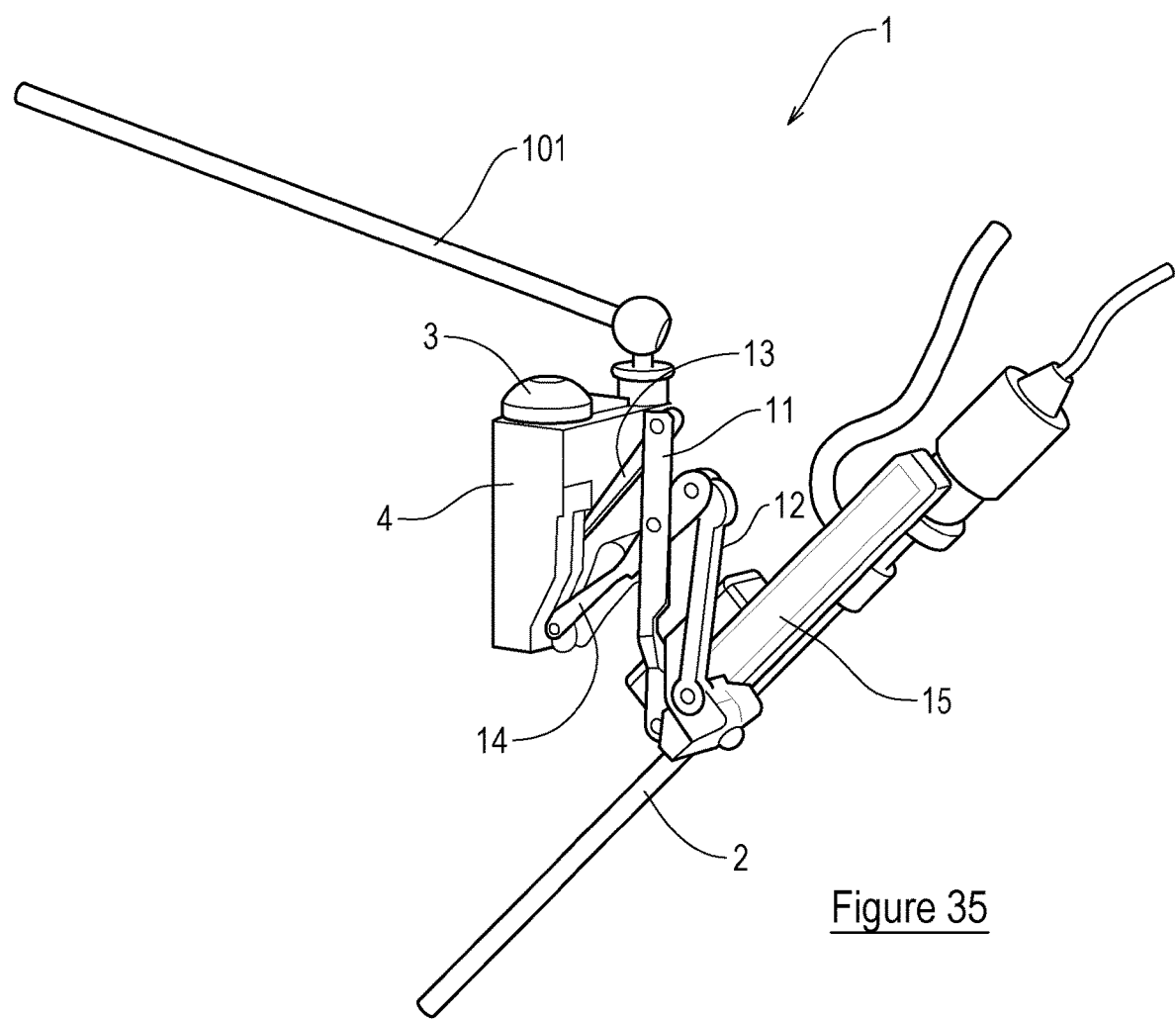
Figure 36:
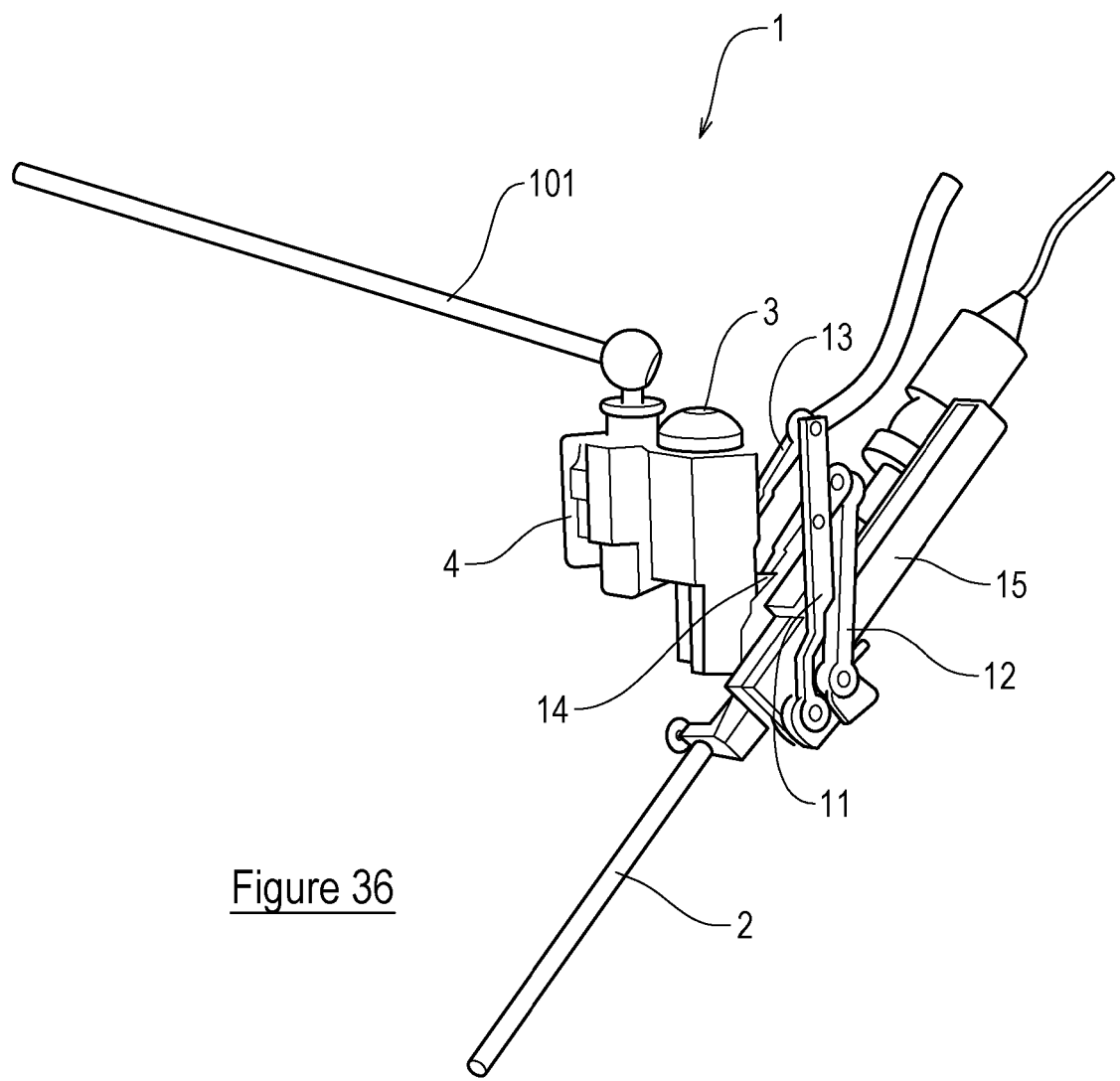
Figure 37:
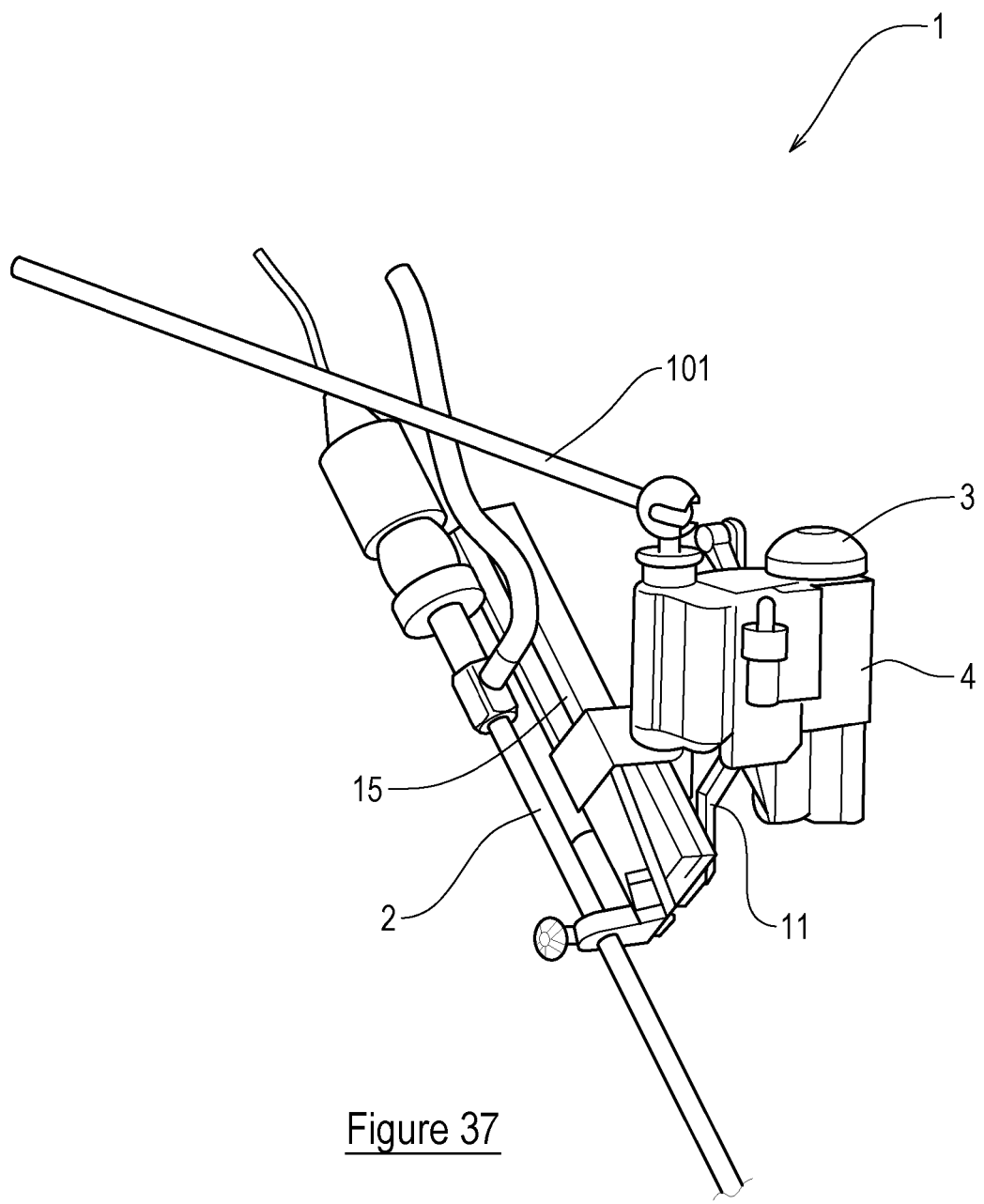

Whilst embodiments have been described, for simplicity with the robotic assistant 1 in a first orientation, the robotic assistant 1 may be provided in other orientations—e.g. perpendicular to the first orientation. In some such orientations, the normal means of the terms pan and tilt, mean that what is described herein as a pan movement is a tilt movement and what has been described herein as a tilt movement is a pan movement. To this end, FIG. 28 shows an embodiment in a different orientation—a sideways orientation.

In some embodiments, a dome 3 may be provided which is configured to house one or more sensors, wherein the or each sensor is configured to receive (and/or sense) an instruction to perform a movement—e.g. a pan operation, a tilt operation, a zoom operation, or the like. The or each sensor may be an optical sensor which is configured to receive an infra-red signal, for example.

In some embodiments, the tilt operation may have a range of 160 degrees which may be generally symmetrical about a plane which is perpendicular to the pan axis.

Whilst embodiments have been described with reference to a surgical assistant 1, it will be appreciated that embodiments may be used for other purposes. Therefore, embodiments include a more general tool holder 1 which may or may not be used in the field of surgical operations.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A tool holder for use as a surgical assistant, the tool holder including:
    first and second beam members;
    a frame;
    at least one linkage member coupled to the frame and the first and second beam members;
    a mounting configuration to hold a tool, the mounting configuration being coupled to the first and second beam members; and
    a drive mechanism mounted with respect to the frame, wherein
    the at least one linkage member and the mounting configuration are coupled to the first and second beam members in a parallelogram configuration,
    the drive mechanism is configured to drive a tilt movement of the mounting configuration with respect to the frame by movement of the first beam member with respect to the second beam member to orient the mounting configuration to a tilt angle, and
    the drive mechanism is configured to drive a pan movement of the tool about a pan axis, the drive mechanism being further configured to orient the pan axis with respect to the frame dependent on the tilt angle the drive mechanism further includes at least one drive motor to drive the pan movement and tilt movement, and the tool holder further includes a mode selection arm which is drivable, by the drive mechanism, between a first position associated with the tilt movement and a second position associated with the pan movement.

2. The tool holder according to claim 1, wherein the at least one linkage member includes a first and a second linkage member.

3. The tool holder according to claim 1, further including:
    one or more brake elements configured to inhibit or substantially prevent movement of the at least one linkage member with respect to the frame.

4. The tool holder according to claim 1, wherein the at least one drive motor is a single motor to drive both the pan and tilt movements.

5. The tool holder according to claim 1, further including a mode changing motor which is configured to change a mode of operation at least one drive motor between a tilt mode of operation and a pan mode of operation.

6. The tool holder according to claim 5, wherein the mode changing motor is associated with a brake element of the drive mechanism which is configured to brake movement of at least part of the drive mechanism when not in a mode changing mode of operation.

7. The tool holder according to claim 1, wherein the mode selection arm is coupled to a carriage member which is configured for rotation with respect to the mode selection arm.

8. The tool holder according to claim 7, wherein a brake element of the drive mechanism is associated with the carriage member and is configured to provide selective braking of the rotational movement between the mode selection arm and the carriage member.

9. The tool holder according to claim 7, wherein the carriage member is configured for rotation with respect to the mode selection arm about a first carriage axis and the carriage member defines a second carriage axis, the second carriage axis being the pan axis about which the pan movement occurs.

10. The tool holder according to claim 9, further including a slide mechanism coupled to the carriage member and the first beam member, wherein the slide mechanism is configured for rotation about the second carriage axis.

11. The tool holder according to claim 10, wherein the slide mechanism is configured to vary in length between a coupling to the carriage member and the first beam member.

12. The tool holder according to claim 1, wherein each of the at least one linkage member is coupled to the frame via a joint mechanism.

13. The tool holder according to claim 12, wherein the joint mechanism is configured to permit rotational movement of the coupled linkage member with respect to the frame about at least two axes.

14. The tool holder according to claim 13, wherein the two axes are perpendicular to each other.

* * * * *